United States Patent [19]

Dear et al.

[11] 4,001,305

[45] Jan. 4, 1977

[54] NEW RF-GLYCOLS CONTAINING TWO PERFLUOROALKYLTHIO GROUPS AND USEFUL COMPOSITIONS THEREFROM

[75] Inventors: Robert Ernest Arthur Dear, Mount Kisco; Robert Allan Falk, New City, both of N.Y.

[73] Assignee: Ciba-Geigy Corporation, Ardsley, N.Y.

[22] Filed: Nov. 12, 1975

[21] Appl. No.: 631,005

Related U.S. Application Data

[63] Continuation-in-part of Ser. No. 439,497, Feb. 4, 1974, Pat. No. 3,935,277.

[52] U.S. Cl. .......................... 260/486 H; 260/399; 260/476 R; 260/485 G; 260/485 P; 260/488 J; 260/609 R
[51] Int. Cl.² .............. C07C 149/20; C07C 149/40
[58] Field of Search ............ 260/486 R, 488 J, 399, 260/485 G, 485 P, 609 R, 476 R

[56] References Cited

UNITED STATES PATENTS 2,961,470   11/1960   Sheppard ...................... 260/609 R

*Primary Examiner*—Lewis Gotts
*Assistant Examiner*—D. R. Phillips
*Attorney, Agent, or Firm*—Joseph G. Kolodny; Edward McC. Roberts; Prabodh I. Almaula

[57] ABSTRACT

Perfluoroalkylthio glycols and esters thereof can be prepared by the free-radical catalyzed addition of a perfluoroalkylthiol to an acetylenic alcohol or ester thereof. The compounds obtained are useful intermediates for the synthesis of fluorochemicals with low free surface energies having oil and water repellent properties. In one embodiment, a perfluoroalkylthio glycol can be reacted with a diisocyanate to obtain a polyurethane containing perfluoroalkylthio groups, which polyurethanes are useful as coatings to provide oil and water repellence to textiles and as additives to plastics to provide mold-release and other desirable properties.

12 Claims, No Drawings

$R_f$-GLYCOLS CONTAINING TWO PERFLUOROALKYLTHIO GROUPS AND USEFUL COMPOSITIONS THEREFROM

This application is a continuation-in-part of application Ser. No. 439,497, filed Feb. 4, 1974, now U.S. Pat. No. 3,935,277, issued Jan. 27, 1976.

DESCRIPTION OF THE INVENTION

This invention relates to novel $R_f$-glycols and derivatives thereof which are useful as intermediates for the synthesis of fluorochemical compounds which possess low free surface energies and provide oil and water repellency. One aspect of this invention relates to a method of making said $R_f$-glycols esters and ethers. Another aspect of this invention relates to $R_f$-containing urethane compositions. One embodiment of this aspect of the invention relates to a reactive composition comprising a mono- or polyisocyanate or isocyanate terminated prepolymer and an $R_f$-glycol or hydroxyl-terminated $R_f$-containing prepolymer. In another embodiment of this aspect, the $R_f$-glycols can be converted to isocyanate-terminated $R_f$-prepolymers which form reactive compositions with alcohols, polyols, $R_f$-glycols, polyol prepolymers and hydroxyl-terminated $R_f$-containing prepolymers. In still another embodiment, the $R_f$-glycols can be used to replace part or all of the hydroxyl component in a urethane composition. In yet another embodiment, the invention relates to a urethane composition containing the residue of at least one $R_f$-glycol. Another aspect of the invention relates to a substrate containing 0.01 to 10% by weight of a fluorine-containing urethane composition, at least part of said fluorine being provided by one or more units derived from the $R_f$-glycols.

The novel $R_f$-glycols and derivatives thereof have the general formula:

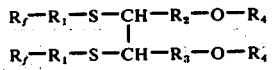

where $R_f$ is straight or branched chain perfluoroalkyl of 1 to 18 carbon atoms or said perfluoroalkyl substituted by perfluoroalkoxy of 2 to 6 carbon atoms, $R_1$ is branched or straight chain alkylene of 1 to 12 carbon atoms, alklenethioalkylene of 2 to 12 carbon atoms, alkyleneoxyalkylene of 2 to 12 carbon atoms or alkyleneiminoalkylene of 2 to 12 carbon atoms where the nitrogen atom contains as a third substituent, hydrogen or alkyl of 1 to 6 carbon atoms, $R_2$ and $R_3$ each independently is straight or branched chain alkylene of 1 to 12 carbon atoms or alkylene (polyoxylakylene) of formula $C_mH_{2m}(OC_kH_{2k})_r$ where m is an integer from 1 to 12, k is an integer from 2 to 6, r is an integer from 1 to 40.

$R_4$ is hydrogen alkyl of 1 to 24 carbon atoms or acyl where said acyl is derived from an aliphatic or aromatic carboxylic acid of up to 24 carbon atoms. Thus, $R_4$ can be hydrogen, alkyl of 1 to 24 carbon atoms, alkanoyl of 1 to 24 carbon atoms, alkenoyl of 1 to 24 carbon atoms or said alkanoyl or alkenoyl substituted by 1 to 3 of chloro, bromo and carboxyl, or said alkanoyl substituted by phenyl or naphthyl, said phenyl or naphthyl being unsubstituted or substituted by 1 to 3 of chloro, bromo, alkyl of 1 to 6 carbon atoms, alkoxy of 1 to 6 carbon atoms, or said alkanoyl substituted by lower acyl or lower acylamino where lower acyl means alkanoyl or alkenoyl of 2 to 6 carbon atoms and the mono- or di-chloro or bromo derivative thereof;

or $R_4$ is benzoyl or benzoyl substituted by 1 to 3 of chloro, bromo, alkyl of 1 to 18 carbon atoms, alkoxy of 1 to 8 carbon atoms or lower acyl or acylamino where lower acyl means alkanoyl or alkenoyl of 2 to 6 carbon atoms, and the mono- or di-chloro or bromo derivative thereof.

Some preferred members of lower acyl are:

chloroacetyl, bromoacetyl, $\beta$-chloropropionyl, $\beta$-bromopropionyl, $\alpha,\beta$-dichloropropionyl, $\alpha,\beta$-dibromopropionyl, acryl, methacryl, $\alpha$-chloroacryl, $\alpha$-bromoacryl, $\alpha,\beta$- or $\beta,\beta$-dichloro- or dibromoacryl, $\beta$-chlorocrotonyl, $\alpha$-chlorocrotonyl, $\beta$-bromocrotonyl, and $\alpha$-bromocrotonyl, Useful compounds are those where $R_f$ is perfluoroalkyl of 6 to 12 carbon atoms or said perfluoroalkyl substituted by perfluoroalkoxy of 2 to 6 carbon atoms, $R_1$ is branched or straight chain alkylene of 2 to 8 carbon atoms, alkylenethioalkylene of 2 to 8 carbon atoms, alkyleneoxyalkylene of 2 to 8 carbon atoms or alkyleneiminoalkylene of 2 to 8 carbon atoms where the nitrogen atom contains hydrogen or methyl as a third substituent;

$R_2$ and $R_3$ are each independently straight or branched chain alkylene of 1 to 4 carbon atoms or alkylene (polyoxyalkylene) of the formula

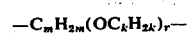

where m is an integer from 1 to 4, k is an integer from 2 to 4, and r is an integer from 1 to 20, and $R_4$ is hydrogen, alkyl of 1 to 24 carbon atoms, alkanoyl of 1 to 24 carbon atoms, alkanoyl of 1 to 6 carbon atoms substituted by phenyl, benzoyl, benzoyl substituted by alkyl of 1 to 6 carbon atoms, or $R_4$ is selected from chloracetyl, bromoacetyl, $\beta$-chloropropionyl, $\beta$-bromopropionyl, $\alpha,\beta$-dichloropropionyl $\alpha,\beta$-dibromopropionyl, acryl, methacryl, $\alpha$-chloroacryl, $\alpha$-bromoacryl, $\alpha,\beta$- or $\beta,\beta$-dichloro or dibromoacryl, $\beta$-chlorocrotonyl, $\alpha$-chlorocrotonyl, $\beta$-bromocrotonyl, or $\alpha$-bromocrotonyl.

Particularly preferred are those compounds where $R_f$ is perfluoroalkyl of 6 to 12 carbon atoms, $R_1$ is alkylene of 2 to 4 carbon atoms, $R_2$ and $R_3$ are both alkylene of 1 or 2 carbon atoms, and $R_4$ is hydrogen alkyl of 6 to 18 carbon atoms or alkanoyl of 6 to 18 carbon atoms.

One group of preferred compounds have the formula

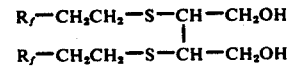

where
- $R_f$ is perfluoroalkyl of 6 to 12 carbon atoms or where
- $R_f$ is perfluoroalkoxyperfluoroalkyl of 4 to 12 carbon atoms, and especially where
- $R_f$ is $(CF_3)_2CFO(CF_2CF_2)_y$- where
- $y$ is an integer from 1 to 6.

Another group of preferred compounds have the formula

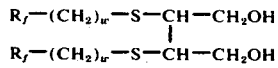

where
- $R_f$ is perfluoroalkyl of 6 to 12 carbon atoms and
- $w$ is an integer from 1 to 8.

A preferred group of alkylene (polyoxyalkylene)-containing $R_f$-glycols have the formula

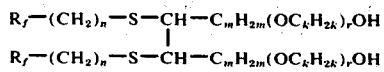

where
- $R_f$ is perfluoroalkyl of 6 to 12 carbon atoms,
- $n$ is an integer from 1 to 12,
- $m$ is an integer from 1 to 4,
- $k$ is an integer from 2 to 4 and
- $r$ is an integer from 1 to 20.

The novel $R_f$-glycols and esters described herein can be obtained by the free-radical catalyzed addition reaction of a perfluoroalkylthiol of formula

to an acetylenic diol or ester of formula

where
- $R_2$ and $R_3$ each is straight or branched chain alkylene of 1 to 12 carbon atoms; said alkylene substituted by one or two of phenyl, cyclohexyl; or an alkylene (polyoxyalkylene) group of formula $C_mH_{2m}(OC_kH_{2k})_r$ where
- $m$ is an integer from 1 to 12,
- $k$ is an integer from 2 to 6,
- $r$ is an integer from 1 to 40, and
- $R_1$ and $R_4$ are as previously defined.

$R_2$ and $R_3$ each preferably is a straight or branched chain alkylene of 1 to 6 carbon atoms; said alkylene substituted by one or two of phenyl and cyclohexyl; or an alkylene (polyoxyalkylene) group of formula $C_mH_{2m}(OC_kH_{2k})_r$ where
- $m$ is an integer from 1 to 4,
- $k$ is an integer from 2 to 4,
- $r$ is an integer from 1 to 20, and
- $R_4$ is preferably hydrogen.

In one embodiment, the acetylenic compounds have the formula

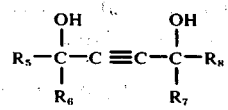

where
- $R_5$, $R_6$, $R_7$ and $R_8$ are selected from hydrogen, alkyl of 1 to 4 carbon atoms, cyclohexyl, and phenyl.

Although $R_2$ and $R_3$ can contain such unsaturated groups as vinyl, allyl and styryl, such groups are not preferred since they compete for the $R_f$-thiol and result in undesirable perfluoroalkyl by-products.

In a particularly preferred embodiment, $R_5$, $R_6$, $R_7$, and $R_8$ are each hydrogen or alkyl of 1 to 4 carbon atoms. Especially preferred is the case where $R_5$, $R_6$, $R_7$, and $R_8$ are selected from hydrogen, and alkyl of 1 to 3 carbon atoms.

In another preferred embodiment $R_6$ and $R_7$ are each hydrogen and $R_5$ and $R_8$ are selected from hydrogen, alkyl of 1 to 4 carbon atoms, cyclohexyl and phenyl.

Physical constants for some of the compounds described above are as follows:

| $R_5$ | $R_6$ | $R_7$ | $R_8$ | °C |
|---|---|---|---|---|
| H | H | H | H | MP 58° |
| $CH_3$ | H | H | $CH_3$ | BP 126–128° at 18 mm |
| $(CH_3)_2CH$ | H | H | $(CH_3)_2CH$ | MP 69° |
| $(CH_3)_2CH-CH_2$ | H | H | $(CH_3)_2CH-CH_2$ | BP 158–160° at 15 |
| $C_6H_{13}$ | H | H | $C_6H_{13}$ | BP 205° at 18mm |
| $C_6H_5$ | H | H | $C_6H_5$ | MP 12° |
| $CH_2=CH-$ | H | H | $CH_2=CH-$ | BP 146 at 15mm |
| $CH_3-CH=CH-$ | H | H | $CH_3-CH=CH-$ | MP 90–92° |
| $C_6H_5-CH=CH-$ | H | H | $C_6H_5-CH=CH-$ | MP 162° |
| $R_5$ | $R_6$ | $R_7$ | $R_8$ | °C |
| $CH_3$ | $CH_3$ | $CH_3$ | $CH_3$ | MP 95° |
| $C_2H_5$ | $CH_3$ | $CH_3$ | $C_2H_5$ | BP 155–160° at 18mm |
| $C_2H_5$ | $C_2H_5$ | $C_2H_5$ | $C_2H_5$ | MP 74° |
| $C_3H_7$ | $CH_3$ | $CH_3$ | $C_3H_7$ | MP 56°–58° |
| $C_3H_7$ | $C_3H_7$ | $C_3H_7$ | $C_3H_7$ | MP 120° |
| $C_6H_5$ | $CH_3$ | $CH_3$ | $C_6H_5$ | MP 163° |
| $C_6H_5$ | $C_6H_5$ | $C_6H_5$ | $C_6H_5$ | MP 193° |

$R_f$-glycols where $R_2$ and $R_3$ are $C_mH_{2m}(OC_kH_{2k})_r$ can be made by converting the original acetylenic diol to the hydroxyalkyl ether, followed by free radical addition of the thiol $R_fR'$—SH. In like fashion the alkyl ethers, where $R_4$ is alkyl, can be prepared, using the Williamson synthesis and known variations thereof.

The $R_f$-esters can be made by alternate routes. $R_f$-glycols can be esterified by well-known synthetic organic methods, such as treatment of the alcohol with a carboxylic acid anhydride, an acyl halide or a carboxylic acid. Alternately, the thiol $R_f$—$R^1$—SH can be added to the acetylenic ester.

The following acetylenic diols and esters are commercially available:

2-butyn-1,4-diol
3,4-dimethyl-1-pentyn-3,4-diol
2,5-dimethyl-3-hexyn-2,5-diol
3-hexyn-2,5-diol
3,6-diethyl-4-octyn-3,6-diol
2,6-dimethyl-4-octyn-3,6-diol
2,3,6,7-tetramethyl-4-octyn-3,6-diol 4,7-dimethyl-5-decyn-4,7-diol
2,4,7,9-tetramethyl-5-decyn-4,6-diol
2-butynediol diacetate perfluoroalkyl thiols useful herein are well documented in the prior art. For example, thiols of the formula $R_fR^1$-SH have been described in a number of U.S. Pat. Nos. including 2,894,991; 2,961,470; 2,965,677; 3,088,849; 3,172,190; 3,544,663 and 3,655,732.

Thus, U.S. Pat. No. 3,655,732 discloses mercaptans of formula $$R_f-R^1-SH$$

where
$R^1$ is alkylene of 1 to 16 carbon atoms and $R_f$ is perfluoroalkyl and teaches that halides of formula $R_f$—$R^1$—hal are well-known; reaction of $R_fI$ with ethylene under free-radical conditions gives $R_f(CH_2CH_2)_nI$ while reaction of $R_fCH_2I$ with ethylene gives $R_fCH_2(CH_2CH_2)_nI$ as is further taught in U.S. Pat. Nos. 3,088,849; 3,145,222; 2,965,659 and 2,972,638.

U.S. Pat. No. 3,655,732 further discloses compounds of formula $R_f$—$R^1$—X—$R''$—SH
where
$R^1$ and $R''$ are alkylene of 1 to 16 carbon atoms, with the sum of the carbon atoms of $R^1$ and $R''$ being no greater than 25; $R_f$ is perfluoroalkyl of 4 through 14 carbon atoms and X is —S— or —NR'''— where $R'''$ is hydrogen or alkyl of 1 through 4 carbon atoms.

U.S. Pat. No. 3,544,663 teaches that the mercaptan $$R_fCH_2CH_2SH$$

where
$R_f$ is perfluoroalkyl of 5 to 13 carbon atoms, can be prepared be reacting the perfluoroalkyl alkylene iodide with thiourea or by adding $H_2S$ to a perfluoroalkyl substituted ethylene ($R_f$—CH=CH$_2$), which in turn can be prepared by dehydrohalogenation of the halide $R_f$—CH$_2$CH$_2$— hal.

The reaction of the iodide $R_f$—$F^1$—I with thiourea followed by hydrolysis to obtain the mercaptan $R_f$—$R^1$—SH is the preferred synthetic route and the reaction is illustrated in Examples 64 and 65. The reaction is applicable to both linear and branched chain iodides. Many useful perfluoroalkoxyalkyl iodides are described in Australian Application 36868 filed Apr. 24, 1968, of general formula $$(CF_3)_2CFO\ CF_2CF_2(CH_2CH_2)_mI$$

where
$m$ is 1–3.

Particularly preferred herein are the thiols of formula $$R_fCH_2CH_2SH$$

where
$R_f$ is perfluoroalkyl of 6 to 12 carbon atoms. These $R_f$-thiols can be prepared from $R_fCH_2CH_2I$ and thiourea in very high yield.

The formation of the $R_f$-glycols and esters proceeds via the formation of intermediates which may be present as byproducts in the $R_f$-glycols and esters. These intermediates have the formula $$R_f-R^1-\underset{\underset{CH-R^3-O-R^4}{\|}}{SC}-R^2-O-R^4$$

and $$R_f-R^1-\underset{\underset{CH-R^2-O-R^4}{\|}}{SC}-R^3-O-R^4$$

Such intermediate formation is considered consistent with the general pathway for the free-radical addition of thiols to acetylenes (Acetylenes and Allenes; T. F. Rutledge, Reinhold Book Corporation, 1969, page 142). That the addition of the thiol to the triple bond is a stepwise reaction proceeding through the intermediates can be shown by reacting the thiol with an excess of the acetylenic diols or esters whereby is obtained the intermediates in high yields.

In the synthesis of the $R_f$-glycols and derivatives thereof described above, it must be emphasized that the addition of $R_f$-thiols to acetylenic alcohols and esters is not equivalent to the reactions described in the literature for the addition of a non-fluorinated thiol to an acetylenic alcohol. When the conventional prior art conditions are employed, it has been found that, although some $R_f$-glycol or ester is produced, the yield is unacceptably low, while the proportions of intermediates (mono-adducts) and disulfides (of the type ($R_f$—$R_1$—S—)$_2$) are unacceptably high. Such reaction conditions as described by A. T. Blomquist and J. Wolinski, J. Org. Chemistry, 23, 551 (1958), utilizing UV radiation and peroxides at room temperature, and requiring reaction periods of 1 to 4 weeks are beyond the limits of commercial acceptability.

The improved process of this invention involves the combination of
a. from 0.5 to 20 percent of a mole of an azo-type free-radical catalyst, preferably from 1 to 10 percent of a mole of catalyst;
b. moderate reaction temperatures, on the order of 40° to about 100° C and
c. a mole ratio of $R_f$-thiol to acetylenic diol or ester of from 2.0 to 2.5 moles of thiol per mole of acetylenic compound.

The reaction temperature and choice of azo-type freeradical catalyst are considered to be mutually dependent. The temperature range of 40° to 100° C is one wherein the formation of undesirable by-products is minimized and wherein the reaction products are stable. In order to achieve a reasonable reaction rate of these temperatures, it is desirable to use an azo-type catalyst that is reactive to a reasonable extent in this temperature range. It is therefore, preferred to use an azo-type free-radical catalyst having a 1-hour half-life temperature of 40° to about 100° C. These compounds are listed below.

| Compound | 1 Hr. Half-Life Temperature ° C | |
|---|---|---|
| 2-t-butylazo-2-hydroperoxy-4-methylpentane | 45° C | |
| 2-t-butylazo-2-cyano-4-methoxy-4-methylpentane | 74° C | |
| Di-t-butyl-4,4'-azobis-(4-cyano-peroxyvalerate) | 80° C | (azo) |
| azobisisobutryonitrile | 81° C | |
| 2-t-butylazo-2-cyano-4-methylpentane | 88° C | |
| 4-t-butylazo-4-cyanovaleric acid | 93° C | (trichlorobenzene) |
| 1,3-dimethyl-3-(t-butylperoxy)-butyl-4-t-butylazo-4-cyanovalerate | 94° C | (azo) |
| t-butyl peroxy-4-t-butylazo-4-cyanovalerate | 94° C | (azo) |
| ethylene bis (4-t-butylazo-4-cyano-valerate) | 94° C | |
| 2-(t-butylazo) isobutyronitrile | 97° C | |
| 4-(4-t-butylazo-4-cyanovaleryloxy)-2-hydroxybenzophenane | 100° C | |
| 2-t-butylazo-2-cyanobutane | 104° C | |

Source:
Commercial Development Department,
Lucidol Chemicals, Buffalo, N.Y.

Other azo-type free-radical catalysts are known and can be used but, because of their higher 1-hour half-life temperatures, are less preferred.

It is preferred to use an azo compound having a 1-hour half-life of from about 75° C to about 90° C and a reaction temperature of from about 60° C to about 80° C. Because of the ease of availability, it is preferred to use azobisisobutyronitrile as the catalyst.

The reaction can be carried out in bulk or in a suitable inert medium which acts to disperse or dissolve the reactants. The bulk reaction, with a solvent medium, is usually preferred. However, if solvents are used, useful solvents include ketones, such as acetone, methyl ethyl ketone and methylisobutyl ketone; esters such as ethyl acetate, butyl acetate, 2-ethylhexyl acetate; hydrocarbons such as hexane, heptane, octane and higher homologs, cyclohexane, benzene, toluene, xylene or blends of aliphatic, cycloaliphatic and aromatic hydrocarbons; alcohols such as ethanol, n-propanol, isopropanol, t-butanol and methyl cellosolve; ethers, both aliphatic and alicyclic including di-n-propyl ether, dibutyl ether and tetrahydrofuran. In addition, chlorinated solvents such as di-chloroethyl ether, ethylene dichloride, perchloroethylene and carbon tetrachloride can be employed.

Preferred solvents are the hydrocarbon solvents. Of the hydrocarbon solvents, the alkanes of 6 to 10 carbon atoms, the benzene hydrocarbons of 6 to 8 carbon atoms and mixtures thereof are preferred. Carbon tetrachloride and ethylene dichloride are useful chlorinated solvents. The data provided in Examples 17–29 indicates that yields are increased and by-product formation decreased when the alkane solvents are used. Commercially available mixtures of paraffinic, naphthenic and benzene hydrocarbon solvents can also be used successfully.

Using the reaction parameters described above, and continuing until reaction is complete, usually after 6 to 10 hours using azobisisobutronitrile at 75° C, there can be effected an 85 to 95% conversion of the $R_f$-thiol to the desired $R_f$-glycol ether or ester. The overall yield can be increased to greater than 95% because unreacted $R_f$—thiol can be recovered and recycleed. The $R_f$-glycols ethers and esters are generally insoluble in aliphatic and aromatic hydrocarbon solvents, while the $R_f$-thiols are soluble in these materials; the unreacted $R_f$-thiol can be readily recovered by washing the reaction product with a suitable hydrocarbon such as heptane or benzene. Alternately, the $R_f$-thiols can be recovered by passing the crude reaction product through a molecular distillation apparatus under conditions such that the $R_f$-glycols and esters pass through while the $R_f$-thiols are volatilized, and recovered.

As indicated above, the $R_f$ can be used to make $R_f$-containing urethane compositions. These urethane compositions have extremely low free surface energies and therefore, possess oil and water repellent properties, as well as mold release and other properties associated with low free surface energy. It should be noted that the urethane compositions of this invention are characterized by the presence of two perfluoroalkylthio groups on adjacent carbon atoms, a characteristic which provides improved oil and water repellent properties over the fluorinated urethane compositions of the prior art. Using the $R_f$-compounds and compositions described herein, it is possible to manufacture molds that display the excellent release properties characteristic of the silicone polymers.

In addition, the compounds where $R_4$ is $C_mH_{2m}(OC_kH_{2k})_r$ are useful as nonionic surfactants, especially where r is an integer from about 5 to about 30.

The esters, where $R_4$ is acyl and the ethers, where $R_4$ is alkyl are useful as additives to synthetic and natural polymers to reduce the surface energy and to provide mold release characteristics.

The diols, where $R_4$ is hydrogen can be used to make a variety of condensation products such as polyesters, polyamides, polycarbonates, polyurethanes and the like. The polyurethanes are particularly preferred.

As used herein the term "urethane composition" means compounds and compositions which contain the characteristic

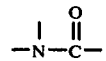

linkage and at least one $R_f$-containing group of formula

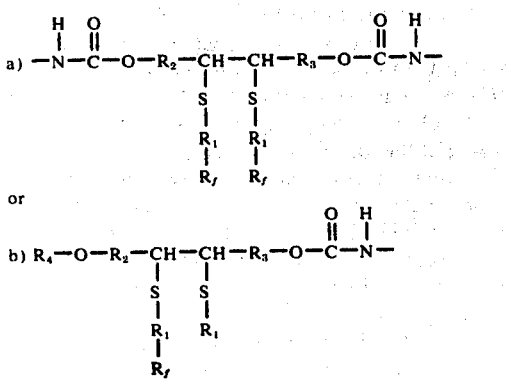

where
$R_f$, $R_1$, $R_2$, $R_3$ and $R_4$ are as previously described.

Preferred urethane compositions include those where $R_f$, $R_1$, $R_2$, $R_3$ and $R_4$ have the configurations previously described as being preferred.

The $R_f$-glycols can be used to make a wide variety of urethane intermediates and end products including hydroxyl and isocyanate-terminated prepolymers, low molecular weight urethane compositions useful to render plastics soil repellent, and high molecular weight compositions useful as elastomers, foams, paints and varnishes, and textile treating compositions. It is also possible to modify these $R_f$-containing urethane compositions so that they are water soluble or self-emulsifiable, a property that is particularly useful in connection with the textile treating compositions.

Polyurethane elastomers generally have remarkable resistance to most solvents including gasoline, aliphatic hydrocarbons and, to some degree, aromatic hydrocarbons. They also exhibit excellent abrasion resistance. By inclusion of the $R_f$-glycol in an elastomer formulation, it is possible to increase the solvent resistance of urethane elastomers. The elastomers generally involve the reaction product of a diisocyanate, a linear long chain diol and a low molecular weight chain extender such as a glycol, diamine or polyol. Today, elastomers are generally prepared by a prepolymer technique whereby a diisocyanate is reacted with a hydroxyl-terminated polyester or polyether to form an isocyanate-terminated prepolymer. This prepolymer is then further reacted (chain extended) with a glycol, diamine or polyfunctional polyol (e.g. trimethylolpropane). Following the chain extension step, the liquid material solidifies and is removed from a mold and cured at elevated temperatures.

Urethane foams are usually prepared from diisocyanates and hydroxyl-terminated polyethers or polyesters. Linear or slightly branced polymers are used to provide flexible foams while more highly branched polymers produce rigid foams. Foaming is often accomplished by including water in the system, the reaction between isocyanate and water providing carbon dioxide for foaming. For rigid foams a low-boiling liquid such as trichlorofluoromethane has been used as a blowing agent.

Appropriate selection of catalysts, stabilizers, surfactants and other additives controls the foam formation, cell size and type, density, cure and the like. By incorporating the $R_f$-glycol into urethane foams, especially molded foams, it is possible to achieve improved mold release properties in rigid, semi-rigid and flexible foams. It is also possible to improve the water and solvent resistance of foams used as insulation.

Incorporation of the $R_f$-glycols into polyurethane coatings such as paints and varnishes improves the water and solvent resistance thereof. Widely used systems include the two-component coatings wherein a non-volatile isocyanate derived from the reaction of tolylene diisocyanate with a polyol such as trimethylolpropane, is reacted with a polyfunctional polyester. Another system in use involves the one-component polyurethane coatings which are based on stable isocyanate-terminated prepolymers obtained from a diisocyanate such as tolylene diisocyanate and a polyfunctional polyether. Such coatings dry by the reaction of the free isocyanate groups with water or atmospheric moisture. The reaction proceeds through the unstable carbamic acid, with $CO_2$ being eliminated, to give primary amine groups which further react with isocyanate groups to form ureas.

Treatment of a textile with a fluorine-containing composition, notably a fluorine-containing polyurethane, provides oil and water-repellent characteristics thereto. Polyurethane compositions containing the residue of the $R_f$-glycol display improved oil and water repellence of textile substrates.

Of the higher molecular weight urethane compositions, linear polymer, obtained by reacting an $R_f$-glycol with an organic diisocyanate, having recurring structural units of formula

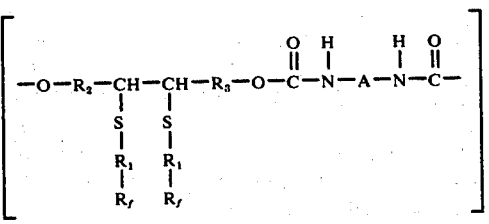

where
$R_f$, $R_1$, $R_2$, and $R_3$ are as previously defined and A is a divalent organic radical, preferably alkylene of 2 to 16 carbon atoms, unsubstituted or substituted phenylene or naphthylene or unsubstituted or substituted biphenylene or bisphenylene
are useful as plastics, fibers, coatings and the like.

However, most urethane compositions that are used commercially to any great extent are copolymers that contain only a relatively small number of urethane linkages. These copolymers are prepared from a variety of segments, typically based on polyethers and polyesters and can have a molecular weight of from 200 to 10,000, generally from about 200 to about 4,000. By the inclusion of an appropriate amount of $R_f$-glycol in the starting materials, it is possible to prepare prepolymers that, when incorporated as part of a urethane composition favorably affect the properties thereof. It is similarly possible to incorporate a desired amount of $R_f$-glycol into the reaction mixture of a conventional prepolymer and an isocyanate so as to obtain conventional urethane compositions containing the divalent residue of the $R_f$-glycol. In the same way, there can be added an $R_f$-containing prepolymer together with or instead of the $R_f$-glycol.

The $R_f$-containing prepolymers can be hydroxy-terminated or isocyanate-terminated and, as indicated, can have a molecular weight as high as 10,000 although a molecular weight of 200 to about 4,000 is more usual.

Hydroxy-terminated prepolymers can be prepared by reacting an excess of a polyhydroxy component with a polyfunctional hydroxy-reactive component such as a polyisocyanate; an isocyanate-terminated prepolymer; a polybasic carboxylic acid, anhydride or acyl halide; phosgene; or a bischloroformate.

The polyhydroxy component can be a polyol, an $R_f$-glycol, a polyether, a polyester, an $R_f$-containing polyether, an $R_f$-containing polyester or mixture thereof.

The polyols are well-known in the urethane art and include

Ethylene glycol
1,3-propanediol
1,4-butanediol
1,5-pentanediol
1,6-hexanediol
1,9-nonanediol
1,10-decanediol
di-, tri-, tetra- and pentaethylene glycol
bis(4-hydroxybutyl) ether
bis(2-hydroxyethyl) thioether
bis(4-hydroxybutyl) thioether
1,4-bis(3-hydroxypropyl) benzene
glycerol
trimethylolpropane
1,2,6-hexanetriol
sorbitol
mannitol
pentaerythritol,
2-ethyl-1,3-butylene glycol
octamethylene glycol
2-ethyl-1,3-hexanediol
dodecamethylene glycol
tetradecamethylene glycol
hexadecamethylene glycol
octadecamethylene glycol The polyol can also contain cycloaliphatic groups, e.g. 1,4-cyclohexane-diol, 1,4-bis(hydroxymethyl) cyclohexane, 4,4'-dihydroxyl-1,1'-dicyclohexyl and the like. If desired, mixtures of polyols can be used.

Polyols in addition to those described above, that are considered especially useful, are those containing tertiary nitrogen atoms which can be quaternized with acids, thereby converting a water-insoluble urethane composition into one that is water soluble or emulsifiable. Generally, an isocyanate-terminated prepolymer having a molecular weight of 200 to 10,000, preferably 400 to 4,000, is reacted with a difunctional tertiary amine to provide a segmented polymer containing tertiary nitrogen atoms. The nitrogen atoms can be quaternized, for example, by alkylation with methyl chloride or dimethyl sulfate to yield a composition that in polar media yields a dispersion in water. The polyammonium polyurethane compositions are obtained even more readily by neutralization of the basic polyurethane composition in a polar organic solvent such as acetone, methyl ethyl ketone, tetrahydrofuran, with a strong (HCl) or preferably weak (pK>4) acid such as the $C_2 - C_9$ alkanoic acids. Acetic acid is especially preferred because the acetic acid evaporates with the water on drying to leave the water-insoluble hydrophobic starting polyurethane composition.

The neutralized polyurethane composition in a polar solvent spontaneously forms a dispersion when water is stirred in. The solvent can thereafter be distilled off to give a solvent-free latex whose film-forming qualities are comparable to those of the organic solution.

In a convenient mode of preparing the water-dispersible basic polyurethane compositions, a polyester or polyether diol is reacted in a non-reactive polar solvent, such as acetone, methyl ethyl ketone, tetrahydrofuran and the like, with an excess of a diisocyanate such as tolylene diisocyanate or, preferably an aliphatic diisocyanate which tends to give non-yellowing urethanes such as dimer acid derived diisocyanate (DDI, commercially available from Quaker Oats Company) or another diisocyanate which is described herein as providing non-yellowing urethanes, and the prepolymer partially chain extended wih an alkyl diethanolamine to yield a urethane composition containing tetiary amino groups. The urethane composition can then be acidified with a solution of aqueous weak acid (pK>4) such as acetic acid; the concentration of acid is not critical. An emulsion immediately forms when this composition is added to water.

The polyurethane compositions can contain from as little as 5 to 800 milliequivalents of ammonium groups per 100 grams of polyurethane composition, preferably from about 50 to about 500 milliequivalents of ammonium groups per 100 grams.

Some useful polyols containing tertiary nitrogen atoms can be represented by the formula

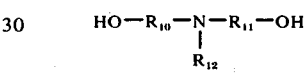

where
$R_{10}$ and $R_{11}$ are alkyl of 2 to 4 carbon atoms or a group of formula

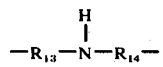

where
$R_{13}$ and $R_{14}$ are alkyl of 2 to 4 carbon atoms
$R_{12}$ is alkyl of 1 to 18 carbon atoms, cyclohexyl, tolyl, xylyl, naphthyl, or with the nitrogen atom forms piperazyl or pyridyl.

Useful polyols that contain tertiary nitrogen atoms include the alkoxylated aliphatic, cycloaliphatic aromatic and heterocyclic primary amines:

N-methyl-diethanolamine
N-butyl-diethanolamine
N-oleyl diethanolamine
N-cyclohexyl-diethanolamine
N-methyl-diisopropanolamine
N-cyclohexyl-diisopropanolamine
N,N-dihydroxyethylaniline
N,N-dihydroxyethyl-m-toluidine
N,N-dihydroxyethyl-p-toluidine
N,N-dihydroxypropyl-naphthylamine
N,N-tetrahydroxyethyl-aminopyridine
dihydroxyethylpiperazine
polyethoxylated butyldiethanolamine
polypropoxylated methyldiethanolamine (molecular wt. 1000)
polypropoxylated methyldiethanolamine (molecular wt. 2000)
polyesters with tertiary amino groups
tri-2-hydroxypropyl-(1)-amine N,N-di-n-(2:3-dihydroxypropyl)-aniline
N,N'-dimethyl-N,N'-bis-hydroxyethylhydrazine
N,N'-bis-hydroxypropylethylenediamine
N,N'-dimethyl-N,N'-bis(hydroxyethyl)-ethylenediamine
11-stearyldiethanolamine
N,N'-bis(hydroxyethyl)-piperazine The $R_f$-glycols can be incorporated in the water-dispersible urethane compositions in an amount sufficient to provide the desired improvement in the surface properties of the polyurethane composition.

Useful polyethers are well-known and widely employed in urethane technology.

The polyethers are generally prepared commercially from lower alkylene oxides e.g. ethylene, propylene and butylene oxide and di- or polyfunctional alcohols. They have a molecular weight of from 400 to 5000. A list of commercially available polyethers, trade names, molecular weight range and suppliers can be found in Volume 11, Polyurethane, page 511, Encyclopedia of Polymer Science and Technology, John Wiley and Sons, Inc., 1969.

Hydroxy-terminated polyesters can be prepared from a polybasic acid, anhydride or aryl halide and a polyol, as described above and/or an $R_f$-glycol.

Useful dicarboxylic acids are those derived from a saturated aliphatic dicarboxylic acid of 2 to 18 carbon atoms or an aromatic dicarboxylic acid of 8 to 18 carbon atoms, e.g. compounds of formula $B(COOH)_2$ where B is preferably alkylene of 0–16 carbon atoms or arylene of 6 to 16 carbon atoms. Such acids include oxalic, malonic, succinic, glutanic, adipic, pirnelic, suberic, azelaic, sebacic, brassylic, thopsic, octadecanedioic, 1,4-cyclohexanedicarboxylic, 4,4'-dicyclohexyl-1,1'-dicarboxylic, phthalic, isophthalic, terephthalic, methylphthalic, chlorophthalic, diphenyl-2,2'-dicarboxylic, diphenyl-4,4'-dicarboxylic, 1,4-naphthalene dicarboxylic, diphenylmethane-2,2'-dicarbosylic, diphenylmethane-3,3'-dicarboxylic, diphenylmethane-4,4'-dicarboxylic acid and the like.

Adipic acid and phthalic anhydride are the most common acid and anhydride. Of the polyols, the most commonly used include ethylene glycol, propylene glycol, 1,2-, 1,3- and 1,4-butylene glycol, 1,6-hexylene glycol, trimethylolpropane, glycerol 1,2,6-hexanetriol and diethylene glycol.

Useful hydroxyl-terminated polyesters can also be derived from natural caster oil and glycerol or from caprolactones and ethylene glycol. Such hydroxy-terminated polyesters have hydroxyl numbers ranging from 40 to 500 and very low acid numbers ranging from 0 to 2.

Hydroxyl-terminated polycarbonates can be obtained by reacting an excess of a polyol with phosgene.

Hydroxy-terminated polybutadienes, or butadienes-tyrenes and butadiene-acrylonitriles are useful herebin, as are hydroxyl containing graft polymers of the polyetherpolyacrylonitrile type.

Any convenient isocyanate can be used to react with the $R_f$-glycol or $R_f$-containing hydroxy-terminated prepolymer. Myriads of useful isocyanates are well-known in the art. Thus, one can use aromatic isocyanates, diisocyanates triisocyanates and polyisocyanates.

Useful aromatic diisocyanates can be represented by the formula

where
A is phenylene that is unsubstituted or substituted by one or two of alkyl of 1 to 4 carbon atoms, alkoxy of 1 to 4 carbon atoms, chloro, bromo and nitro naphthylene that is unsubstituted or substituted by one or two of alkyl of 1 to 4 carbon atoms, chloro, bromo and nitro or where
A is a group of formula

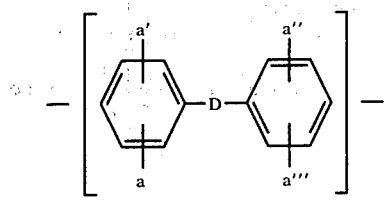

where
D is a direct bond, oxygen, methylene or ethylene and
$a$, $a'$, $a''$ and $a'''$ each independently is hydrogen, alkyl of 1 to 4 carbon atoms alkoxy of 1 to 4 carbon atoms, chloro or bromo Aromatic triisocyanates can be represented by the formula

where
B is the benzene or toluene group.

Aromatic di- and triisocyanates as described above include -
Tolylene diisocyanate (TDI) (all isomers),
4,4'-diphenylmethane diisocyanate (MDI)
Tolidine diisocyanate
Dianisidine diisocyanate
m-Xylylene diisocyanate
p-Phenylene diisocyanate
m-Phenylene diisocyanate
1-Chloro-2,4-phenylene diisocyanate
3,3'-Dimethyl-4,4'-bisphenylene diisocyanate
3,3'-Dimethoxy-4,4'-bisphenylene diisocyanate
4,4'-Bis(2-methylisocyanatophenyl) methane
4,4'-bisphenylene diisocyanate
4,4'-Bis(2-methoxyisocyanatophenyl) methane
1-nitro-phenyl-3,5-diisocyanate
4,4'-diisocyanatodiphenyl ether
3,3'-dichloro-4,4'-diisocyanatodiphenyl ether
3,3'-dichloro,4,4'-diisocyanatodiphenyl methane
4,4'-diisocyanatodibenzyl
3,3'-dimethyl-4,4'-diisocyanatodiphenyl
3,3'-dimethoxy-4,4'-diisocyanatodiphenyl
2,2'-dimethyl-4,4'-diisocyanatodiphenyl
2,2'-dichloro-5,5'-dimethoxy-4,4'-diisocyanatodiphenyl
3,3' dichloro-4,4'-diisocyanatodiphenyl
benzene-1,2,4-triisocyanate
benzene-1,3,5-triisocyanate
benzene-1,2,3-triisocyanate
toluene 2,4,6-triisocyanate
toluene 2,3,4-triisocyanate
1,2-naphthalene diisocyanate
4-chloro-1,2-naphthalene diisocyanate
4-methyl-1,2-naphthalene diisocyanate
1,5-naphthalene diisocyanate
1,6-naphthalene diisocyanate 1,7-naphthalene diisocyanate
1,8-naphthalene diisocyanate
4-chloro-1,8-naphthalene diisocyanate
2,3-naphthalene diisocyanate
2,7-naphthalene diisocyanate
1,8-dinitro-2,7-naphthalene diisocyanate
1-methyl-2,4-naphthalene diisocyanate
1-methyl-5,7-naphthalene diisocyanate
6-methyl-1,3-naphthalene diisocyanate
7-methyl-1,3-naphthalene diisocyanate
polymethylene polyphenyl isocyanate and
co-products of hexamethylene diisocyanate and
tolylene diisocyanate Useful aliphatic diisocyanates include those of general formula $$A(NCO)_2$$

where
A is alkylene of 2 to 16 carbon atoms.
Useful aliphatic polyisocyanates include -
1,2-ethane diisocyanate
1,3-propane diisocyanate
1,4-butane diisocyanate
2-chloropropane-1,3-diisocyanate
pentamethylene diisocyanate
propylene-1,2-diisocyanate
1,6-hexane diisocyanate
1,8-octane diisocyanate
1,10-decane diisocyanate
1,12-dodecane diisocyanate
1,16-hexandecane diisocyanate and
other aliphatic diisocyanates such as
1,3-cyclohexane diisocyanate
1,4-cyclohexane diisocyanate
cyclohexane triisocyanate
4,4'-methylene bis(cyclohexyl) isocyanate Additionally, the following diisocyanates are particularly preferred because urethane compositions made therefrom tend to be non-yellowing:
1,6-hexamethylenediisocyanate (HDI)
2,2,4- and 2,4,4-trimethylhexamethylenediisocyanate (TMDI)
dimeracid derived diisocyanate (DDI) obtained from dimerized fatty acids, such as
linoleic acid 4,4'-dicyclohexylmethane diisocyanate (hydrogenated MDI)
isophorone diisocyanate
3-isocyanatomethyl-3,5,5-trimethylcyclohexylisocyanate
lysine methyl ester diisocyanate (LDIM)
bis(2-isocyanatoethyl) fumerate (FDI)
bis(2-isocyanatoethyl) carbonate Other useful isocyanates include polyisocyanates, particularly triisocyanates which are readily obtained by the reaction of an excess of the corresponding diisocyanate with water according to the following equation:

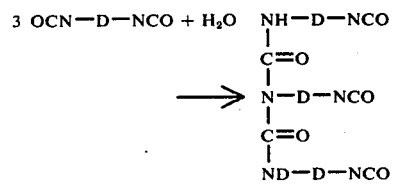

where
D is the residue of a diisocyanate as described above; additional polyisocyanates include polymethylene polyphenylisocyanate (PAPI) and tris-(isocyanatophenyl) thiophosphate (Desmodur R$_f$).

Additional isocyanate components can be prepared by reacting an excess of a diisocyanate as described above with a suitable hydroxyl component, such as a polyol as described above or an R$_f$-glycol as described herein, or combination thereof, to obtain an isocyanate-terminated prepolymer.

In addition to the polyisocyanates, useful urethane compositions can be obtained from the aliphatic and aromatic monoisocyanates. The low molecular weight urethane compositions obtained by reacting an R$_f$-glycol with a monoisocyanate are useful to impart soil and mold-release properties to a variety of natural and synthetic polymers.

Some useful aromatic monoisocyanates include -
2-fluorophenyl isocyanate
3-fluorophenyl isocyanate
4-fluorophenyl isocyanate
m-fluorosulfonylphenyl isocyanate
trans-2-phenylcyclopropyl isocyanate
m-tolyl isocyanate
p-tolyl isocyanate
α,α,α-trifluoro-o-tolyl isocyanate
α,α,α-trifluoro-m-tolyl isocyanate
p-bromophenyl isocyanate
2,5-dimethylphenyl isocyanate
o-ethoxyphenyl isocyanate
p-ethoxyphenyl isocyanate
o-methoxyphenyl isocyanate
m-methoxyphenyl isocyanate
p-methoxyphenyl isocyanate
1-naphthyl isocyanate
o-nitrophenyl isocyanate
m-nitrophenyl isocyanate
p-nitrophenyl isocyanate
p-phenylazophenyl isocyanate
o-tolyl isocyanate Useful aliphatic monoisocyanates include such alkyl isocyanates of 1 to 16 carbon atoms as
methyl isocyanate
ethyl isocyanate
n-propyl isocyanate
n-butyl isocyanate
t-butyl isocyanate
hexyl isocyanate
octyl isocyanate
dodecyl isocyanate
octadecyl isocyanate
hexadecyl isocyanate
and mixtures thereof, as well as cyclohexyl isocyanate.

Isocyanate-terminated prepolymers typically having a molecular weight of from 200 to about 4000 can be prepared by reacting an excess of an isocyanate component with a polyhydroxy component. The isocyanate component can be a diisocyanate or polyisocyanate as previously described, or can be a low molecular weight isocyanate-terminated prepolymer.

The hydroxy component can be one or more of a polyol, polyester, polyether, polycarbonate and R$_f$-glycol, all as described previously.

It can be seen that the properties of ultimate urethane compositions can be modified by appropriate modifications in the compositions of the prepolymers.

In addition to the formation of the urethane compositions described above, the $R_f$-glycols described herein can be converted to the corresponding bischloroformate by treatment with chlorocarbonyl pyridinium chloride:

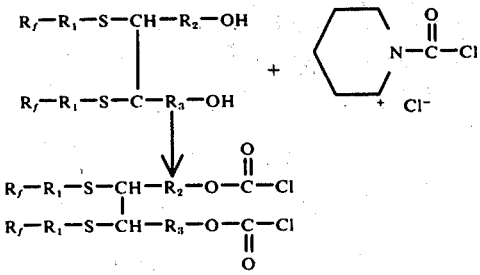

which in turn can be reacted with an appropriate amine to yield a urethane compositin:

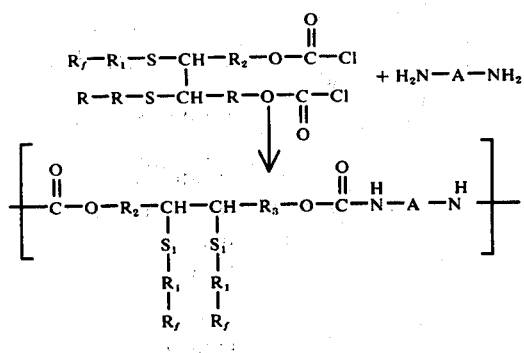

where

A is a divalent organic radical as previously described.

The reaction between the isocyanate component and the hydroxyl component can be carried out in bulk, i.e., without solvent, or in the presence of non-reactive, anhydrous, organic solvents. Solvent media in which the reaction can be carried out include ketones, such as acetone, methyl ether ketone and methylisobutyl ketone; esters such as ethyl acetate, butylacetate, 2-ethyl-hexyl acetate; hydrocarbons such as hexane, haptane, octane and higher homologs, cyclohexane, benzene, toluene, xylene or blends of aliphatic, cycloaliphatic and aromatic hydrocarbons. It is also possible to employ ethers, both aliphatic and alicyclic including di-n-propyl ether, di-butyl ether, tetrahydrofuran and the diethers of polyalkylene oxides. In addition, chlorinated solvents such as dichloroethyl ether, ethylene dichloride, perchloroethylene and carbon tetrachloride can be used.

Among the solvents listed, the water miscible solvents such as acetone and methyl ethyl ketone are most important since they allow conversion of $R_f$-urethanes into water soluble $R_f$-urethanes as previously described.

In all cases, the solvents should be anhydrous to avoid urea formation.

The reaction can, if desired, be catalyzed and those catalysts conventionally employed in the urethane art are useful herein. Useful catalysts fall principally in two groups - a. amino compounds and other bases:
triethylamine and other trialkylamines
triethylenediamine
1,4-diaza-2,2,2-bicyclooctane
N-(lower) alkyl morpholines
N,N,N',N'-tetra-methylethelenediamine
N,N,N',N'-tetramethyl-1,3-butanediamine
N,N,N',N'-substituted piperazines
dialkylalkanolamines
benzyltrimethylammonium chloride b. organometallic and inorganic compounds:
cobalt naphthenate
stannous chloride
stannous actoate
stannous oleate
dimethyl tin dichloride
di-n-butyltin dilaurlmercaptide
tetra-n-butyl tin
trimethyl-tin hydroxide
di-n-butyltindilaurate Such catalysts may be used singly or in combination with each other. Beneficial synergistic catalysis may occur when combinations are used.

While it is possible to carry out the reaction without the use of a catalyst, it is preferable for reasons of economy and to assure a complete reaction, to utilize one or more catalysts as listed in amounts ranging from 0.001 to 1% based on the weight of the reactants. It is similarly advantageous to carry out the urethane synthesis at elevated temperature, usually between room temperature and 120° C and preferably at 60° to 80° C to obtain a complete reaction between 0.5 to 8 hours reaction time.

The reaction can be easily followed by titration of the isocyanate group or by IR analysis.

The determination of the critical surface tension ($\gamma_c$) in dynes per centimeter shows that the free surface energy of a polyurethane is lowered if the novel $R_f$-glycols are incorporated into the urethane chain.

The critical surface tensions ($\gamma_c$) are determined be contact angle measurements as described by W. Zisman, Contact Angles, Advances in Chemistry, No. 43, ACS Publications, Washington, D.C., 1964.

The usefulness of the polyurethane compositions is, however, conveniently shown by measuring the oil, water and soil repellency ratings of substrates such as fabrics, paper, leather, etc. which are treated with solutions or emulsions of the novel urethane compositions.

As already indicated, the urethane compositions of the invention are highly effective for imparting oil and water repellent properties to substrates to which they are applied and coatings of these polymers may be prepared by any of the well-known techniques. When prepared by bulk or suspension polymerization techniques, these urethane compositions can be applied, for example, from a dilute solution in suitable a solvent such as the fluoroalkanes, fluorochloroalkanes, fluoroalkyl substituted aromatics, alkylesters of perfluoroalkanoic acids, chlorinated alkanes or aromatics, hydrocarbon aromatics, ketones, esters and others. Concentrations of the fluorinated polymer in the solvent can be adjusted to provide an amount of urethane composition deposited on the substrate sufficient to provide oil and water repellency. This amounts typically to a deposit of from 0.01 to 10%, preferably from 0.1 to 1%, of urethane composition, based on the weight of substrate. If the urethane composition is obtained as an aqueous latex or emulsion, the system can be diluted with water or other appropriate diluent to similarly provide an amount of urethane ranging from 0.01 to 10% of the weight of substrate deposited thereon.

The urethane solution or latex may be applied by any of the known techniques such as by dipping, spraying, brushing, padding, roll coating or by any desired combination of such techniques. The optimum method of application will depend principally on the type of substrate being coated.

Coatings of the urethane compositions of the invention may be applied to any desired substrate, porous or non-porous. They are particularly suited for application to porous materials such as textiles, leather, paper, wood, masonry, unglazed porcelain and the like to provide valuable oil and water repellency properties. However, they may also be applied to non-porous materials such as metals, plastics, glass, painted surfaces and the like to provide similar oil and water repellency properties. More specifically the urethane compositions of the invention act as levelling, wetting and spreading agents in formulations designed for application to floors, furniture and automobiles. In such applications a protective oil and water repellent film is left on the treated object after the removal of the bulk of the material. Such levelling, wetting, spreading and film forming properties are also useful in a. formulations for cleaning glass and other hard, non-porous materials
b. hair care products such as rinses, shampoos and hair sprays
c. paint, stain and varnish formulations for application to wood, masoning and ceramics.

In the treatment of paper the urethane compositions may be present as an ingredient in a wax, starch, casein, elastomer, or wet strength resin formulation. Aqueous emulsions of the urethane compositions are especially useful in the treatment of paper. By mixing the urethane compositions in an aqueous or oil type paint formulation, it may be applied effectively to unpainted asbestos siding, wood, metal and masonry. In the treatment of floors and tile surfaces and like substrates, and urethane compositions may be applied by their incorporation in an emulsion or solution.

Because of the ability of the surfaces treated with these urethane compositions to withstand abrasive action, the advantages incident to the repellency to oil and water and their resistance to soiling imparted by coating them with the urethane compositions of this invention, preferred classes of articles to be treated are papers and textiles. Illustrative papers are carbonizing tissue, wallpaper, asphalt laminates, liner board, cardboard and papers derived from synthetic fibers.

For application to textile materials such as fabrics woven and non-woven, fibers, films, yarns, cut staple, thread etc. or articles made from fabrics, fibers, films, yarns, etc. the urethane compositions of the invention are preferably prepared as aqueous latices or emulsions which are then diluted, preferably with water and applied to the textiles from pad baths which may contain other treating materials. In accordance with this technique, the fabric or the textile material is passed through the bath, passed through squeeze rolls adjusted to leave the desired amount of the latex on the fabric, dried at a temperature of about 25° to 125° C and then cured in a curing oven at a temperature in the range of from 120° to 195° C for 0.2 to 20 minutes. The weight of urethane composition deposited on the fabric may range from 0.01 to 10% of the weight of fabric. Preferably, very small amounts are used in the range of 0.1 to 1%, often from 0.1 to 0.5% to give high degrees of water and oil repellency. Any types of textile materials, such as cotton, wool, fiber glass, silk, regenerated cellulose, cellulose esters, cellulose ethers, polyesters, polyamides, polyolefins, polyacrylonitrile, polyacrylic esters, inorganic fibers, etc. either along or blended in any combination may be successfully coated with the urethane compositions of the invention. The resulting textile material will be found to be repellent to water and oil, and the textile material will retain its resistance to such agents even after many launderings and dry cleanings.

It will be often advantageous to use the urethane compositions of the invention in combination with conventional finishes, such as mildew preventatives, moth resisting agents, crease resistant resins, lubricants, softeners, fat liquors, sizes, flame retardants, antistatic agents, dye fixatives and water repellents.

The invention described above is illustrated by the following examples:

Examples 1 to 46 illustrate the preparation of the $R_f$-glycols and esters.

Examples 47 to 63 illustrate the preparation of urethane compositions and the present, practical utility of such compositions.

Examples 64 and 65 illustrate the preparation of the $R_f$-thiols.

EXAMPLE 1

2,3-Bis(1,1,2,2-Tetrahydroperfluorodecylthio)-butane-1,4-diol

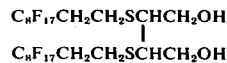

2-Butyn-1,4-diol (1.1g; 0.013 mole) and 1,1,2,2-tetrahydroperfluorodecanethiol (13.64g; 0.028 mole) were stirred together in 16 ml 2-butanone with 0.4g azobisisobutryonitrile (ABN) catalyst. The solution was heated to 83° – 85° for 4 hours, then a further 0.4g of catalyst was added and heating and stirring were continued for a total of 24 hours. After cooling, the solvent was removed by evaporation and the product was recrystallized from benzene to give 8.28g of the desired product (61% conversion). Further purification was effected by distillation of the material (b.p. 180° – 204° at 0.6mm Hg) and final recrystallization from benzene. The pure product melted at 110° – 112°. The infrared spectrum showed OH stretching frequency at 3370 cm$^{-1}$; CH stretching frequency at 2938 and 2878 cm$^{-1}$ and CF stretching frequency from 1330 to 1100 cm$^{-1}$.

The structure was confirmed by nmr examination, which showed signals at:

2.0 – 3.4 ppm, —CH$_2$CH$_2$S— and OH (110H);
3.8 ppm, OCH$_2$ (4H); and 4.3 ppm, SCH(2H).

Analysis for C$_{24}$H$_{16}$F$_{34}$O$_2$S$_2$ Calculated: C, 27.55; H, 1.54; F, 61.73; Found: C, 27.54; H, 1.67; F, 61.46.

EXAMPLE 1a

2,3-Bis(1,1,2,2-Tetrahydroperfluorodecylthio)butyl-1,4-Dimethacrylate

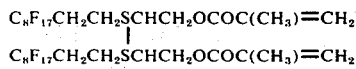

A 50 ml flask was charged with 2,3-Bis(1,1,2,2,-tetrahydroperfluorodecylthio) butane-1,4-diol (10.46 g; 0.01 mole), pyridine (1.58 g; 0.02 mole) and a mixture of 15 ml heptane and 10 ml methylethyl ketone. The solid diol was dissolved with warming to 70° and continuous stirring. Methacrylyl chloride (2.00 g; 0.02 mole) was added over a 30 minute period, under nitrogen. A white solid gradually precipitated from the liquor. To ensure complete reaction the mixture was stirred at 70° for 8 hours. All solids were removed by filtration and the solvents were stripped under reduced pressure. Purification of the crude dimethacrylate on neutral alumina gave 7.2 g product (61.1% of theory) as a white, waxy solid.

The structure was confirmed by spectroscopic examination. Infrared bands were observed at 1735cm$^{-1}$ (C=O stretching frequency) and 1637cm$^{-1}$ (C=C stretching frequency). Nmr showed peaks at 1.9 ppm (6H) CH$_3$; 2.0-3.3 ppm (10H) C$_8$F$_{17}$CH$_2$CH$_2$SCH; 4.35 ppm (4H) OCH$_2$; 5.58 ppm (2H) H trans to C=O; 6.1 ppm (2H) H cis to C=O. Nmr and GLC examination also showed the presence of a small amount of unreacted starting diol, which was difficult to remove. For this reason no true elemental analyses could be obtained.

On standing the monomer spontaneously polymerized to a brittle solid.

EXAMPLE 1b

2,3-Bis(1,1,2,2-Tetrahydroperfluoroalkylthio)butyl-1,4-Dimethacrylate

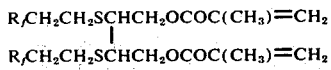

R$_f$ = mixture of C$_6$F$_{13}$; C$_8$F$_{17}$; C$_{10}$F$_{21}$ 2,3-bis(1,1,2,2-tetrahydroperfluoroalkylthio)butane-1,4-diol (40 g; 0.038 mole) was converted to its dimethacrylate by treatment with methacrylyl chloride (8.5 g; 0.082 mole) and pyridine (6.5 g; 0.082 mole) in heptane/methyl ethyl ketone solvent at 70° for 8 hours. Isolation and purification of the product gave 29 g mixed dimethacrylate, as an off-white waxy solid. The structure was confirmed by infrared and nmr spectroscopy. Infrared showed stretching frequencies at 1735cm$^{-1}$ (C=O) and 1638cm$^{-1}$ (C=C). Nmr signals were at 1.9 ppm (6H) CH$_3$; 2.0-3.34 ppm (10H) CH$_2$; 4.35 ppm (4H) OCH$_2$; 5.59 ppm (2H) H trans to C=O; 6.12 ppm (2H) H cis to C=O.

EXAMPLE 2

2,3-Bis(1,1,2,2-Tetrahydroperfluoroalkylthio)-butane-1,4-diol

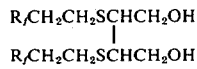

a. Solvent Free Process

In a 500 ml Morton flask, 400g (0.8 mole) 1,1,2,2-tetrahydroperfluoalkanethiol (similar to that described in Example 3, but having an average molecular weight of 500) was mixed with 327g (0.38 mole) 2-butyn-1,4-diol. With moderate stirring the flask was heated to 75° under nitrogen by means of an external oil bath. Azobisisobutyronitrile catalyst (ABN) was added in 5 equal portions of 1.32g each, at 25 minute intervals (total catalyst = 6.6g; 0.04 mole or 5 mole % based on thiol). After the second catalyst addition, an exothermic reaction was noted, which took the reaction temperature to 78° for a period of approximately 1 hour. The course of the reaction was followed by periodically removing samples and analysing them by gas-liquid chromatography (GLC). This showed that after 6½ hours no further reaction was occurring. The composition of the crude reaction product was (area %) thiol (R$_f$CH$_2$CH$_2$SH) 6.2; mono addition product

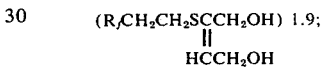

diaddition product

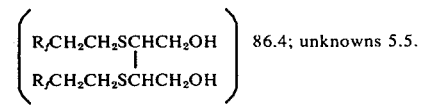

86.4; unknowns 5.5.

The crude product was purified by passage through a falling film molecular distillation apparatus at 110° and 8mm Hg. giving 352g. (85.0% conversion) product consisting of 1.2% thiol, 1.5% monoaddition product, 93.0% diaddition product and 4.3% unknowns. Recovery of unreacted thiol was 34g, bringing the overall yield (conversion and recovery) to 93.5%.

b) Solvent Process

In a 2 liter Morton flask 1,1,2,2-tetrahydroperfluoroalkanethiol (as defined in Example 3) (483g; 1.0 mole) and 2-butyn-1,4-diol (43.05g; 0.5 mole) were mixed in 500 ml heptane. The system was deoxygenated with nitrogen bubbling below the liquid surface and was then heated to 75° with a blade stirrer rotating at high speed. Azobisisobutyronitrile catalyst (ABN) was added in ten portions of 1.64g each over a 5 hour period. The reaction was continued for a total of 20 hours. During this time the upper part of the flask not covered by the heating mantle was insulated with glass wool to prevent the deposition of the forming product on the walls. The reaction mixture was cooled, with stirring, to allow the product to crystallize. Filtration and drying at 40° and 0.5mm Hg permitted the recovery of 441.7g product (83.7% conversion). From the filtrate and the material removed during the pumping operation 61.2g unreacted thiol were obtained. The overall yield was 96.4%. The product melted over the range 73° – 94°. Gas chromatographic examination showed it to be the dialkyl diol with no trace of the monoaddition product.

EXAMPLES 3–7

Further examples of the free radical addition of 1,1,2,2-tetrahydroperfluoroalkanethiol to 2-butyn-1,4-diol are shown below. Except where indicated, $R_f$ is a mixture of perfluoroalkyl chains $C_6F_{13}$, $C_8F_{17}$ and $C_{10}F_{21}$.

reaction was occurring. The crude product was washed with benzene, filtered and dried to give 69.5g product (81.9% of theory). A small sample was further recrystallized and had m.p. 84° – 88°.

The infrared spectrum showed strong O-H stretching frequency at 3300 cm$^{-1}$ and characteristic C-F bands at 1100 – 1300 cm$^{-1}$.

Nmr showed: 2.0-2.6 ppm, CFCH$_2$ and OH (6H); 2.85 ppm, SCH$_2$(4H); 3.1 ppm, SCH(2H); and 3.9 ppm, OCH$_2$(4H). Equivalent wt: Calc. 389; found 388.

EXAMPLES 3 to 7

$$R_fCH_2CH_2SCHCH_2OH$$
$$|$$
$$R_fCH_2CH_2SCHCH_2OH$$

| Example | $R_fCH_2CH_2SH$ | HOCH$_2$C≡CCH$_2$OH | Solvent | ABN | Product | Recovered Thiol | Conversion | % Yield |
|---|---|---|---|---|---|---|---|---|
| 3 | 9.6 g$^a$; 0.02 m | 0.86 g; 0.01 m | Amsco 46$^b$ | 328 mg | 4.53 g | — | 43.2 | — |
| 4 | 48.0 g$^a$; 0.10 m | 4.2 g; 0.05 m | Heptane | 1.6 g | 40.34 g | 7.44 g | 77.3 | 92.8 |
| 5 | 96.6 g; 0.20 m | 8.61 g; 0.10 m | Amsco 46 | 3.28 g | 74.8 g | — | 76.7 | — |
| 6 | 289.8 g; 0.60 m | 25.8 g; 0.30 m | Heptane | 9.84 g | 254.1 g | 43.0 g | 80.6 | 94.2 |
| 7 | 289.8 g; 0.60 m | 25.8 g; 0.30 m | Heptane | 9.84 g | 254.4 g | 58.6 g | 80.6 | 99.2 |

$^a$C$_8$F$_{17}$CH$_2$CH$_2$SH used.
$^b$A hydrocarbon solvent sold by American Mineral Spirits Co. containing 42.4% paraffins, 39.4% naphthenes and 18.2% aromatics.

EXAMPLE 8

2,3-Bis(1,1,2,2-Tetrahydroperfluorodecylthio)-butane-1,4-diol $$C_8F_{17}CH_2CH_2SCHCH_2OH$$
$$|$$
$$C_8F_{17}CH_2CH_2SCHCH_2OH$$

The example shows that the addition may be carried out thermally, without the need for added catalyst.

1,1,2,2-Tetrahydroperfluorodecanethiol (4.8g; 0.01 mole) and 2-butyn-1,4-diol (0.43g; 0.05 mole) were sealed in an ampoule, under nitrogen, with no solvent. The reagents were stirred at 158° for 20 hours during which period a hard, light brown solid formed. Gas chromatographic examination showed this to be 2,3-bis(1,1,2,2-tetrahydroperfluorodecylthio)-butane-1,4-diol. The mono addition product was not formed. The product was purified by crystallization from benzene, and then melted at 105° – 109°. The infrared and nmr data were identical to that obtained for the product of Example 1.

EXAMPLE 9

2,3-Bis(4-Heptafluoroisopropoxy-1,1,2,2-tetrahydroperfluorobutylthiol)-butane-1,4-diol $$(CF_3)_2CFOCF_2CH_2CH_2SCHCH_2OH$$
$$|$$
$$(CF_3)_2CFOCF_2CHCFCH_2SCHCH_2OH$$

4-Heptafluoroisopropoxy-1,1,2,2-tetrahydroperfluorobutanethiol (80g; 0.229 mole) was stirred at 74° with 2-butyn-1,4-diol (9.39g; 0.109 mole) under nitrogen. Azobisisobutyronitrile catalyst (1.88g; 0.0114 mole) was added in 5 equal portions at intervals of 25 minutes. After 10 hours GLC indicated that no further Analysis for C$_{18}$H$_{16}$F$_{22}$O$_4$S$_2$. Calculated: C, 27.77; H, 2.07; F, 53.69, Found: C, 28.03; H, 2.03; F, 53.32.

EXAMPLE 10

2,3-Bis(Heptafluoroisopropyl-1,1,2,2-tetrahydroperfluoroalkanethio) butane-1,4-diol $$(CF_3)_2CFO(CF_2CF_2)_mCH_2CH_2SCHCH_2OH$$
$$|$$
$$(CF_3)_2CFO(CF_2CF_2)_mCH_2CH_2SCHCH_2OH$$
$$m = 3 \text{ or } 4$$

ω-Heptafluoroisopropoxy-1,1,2,2-tetrahydroperfluoroalkanethiol [(CF$_3$)$_2$CFO(CF$_2$CF$_2$)$_m$CH$_2$CH$_2$SH] (consisting of 73% m = 3 homolog and 27% m = 4 homolog) (80g; 0.14 mole) was added to 2-butyn-1,4-diol (5.72g; 0.067 mole), using ABN catalyst (1.15g; 0.007 mole) in the manner described in the previous example. In this case the crude product was purified by passage through a molecular distillation apparatus. This gave 69.7g product and 12.2g recovered thiol. Conversion is thus 83.9% and yield is 99.2% based on starting thiol. The waxy product had a melting point of approximately 37° C. Its nmr and infrared spectra were very similar to those of the preceding example. GLC examination showed that the product was a mixture of three products, formed from the two original thiols. In area % there were: m = 3,3 43.3%; m = 3,4 40.9%; m = 4,4 15.80%.

Analysis: Calculated: on the basis of wt. % = area %. C, 26.36; H, 1.29; F, 62.07; Found: C, 27.37; H, 1.39; F, 61.19.

EXAMPLES 11 to 13

Addition of available thiols to commercial acetylenic alcohols and esters is illustrated by Examples 11 to 13. In each case a free radical catalyzed addition of 2 moles of thiol to 1 mole acetylenic alcohol is involved. The experimental procedure is as described in Example 2a.

EXAMPLES 11 to 13

| Example | Thiols | Alcohol or Ester | Product |
|---|---|---|---|
| 11 | 2 C$_8$F$_{17}$(CH$_2$)$_4$SH | + HOCH$_2$C≡CCH$_2$OH | C$_8$F$_{17}$(CH$_2$)$_4$SCHCH$_2$OH<br>\|<br>C$_8$F$_{17}$(CH$_2$)$_4$SCHCH$_2$OH |
| 12 | 2 C$_8$F$_{17}$CH$_2$CH$_2$SH | + CH$_3$CH(OH)C≡CCH$_2$OH | C$_8$F$_{17}$CH$_2$CH$_2$SCHCH(OH)CH$_3$<br>\|<br>C$_8$F$_{17}$CH$_2$CH$_2$SCHCH(OH)CH$_3$ |
| 13 | 2 C$_8$F$_{17}$(CH$_2$)$_4$SH | + H(OCH$_2$CH$_2$)$_n$OCH$_2$C≡CCH$_2$O(CH$_2$CH$_2$O)$_n$H | C$_8$F$_{17}$(CH$_2$)$_4$SCHCH$_2$O(CH$_2$CH$_2$O)$_n$H<br>\|<br>C$_8$F$_{17}$(CH$_2$)$_4$SCHCH$_2$O(CH$_2$CH$_2$O)$_n$H | n = 1 average

EXAMPLE 14

2,3-Bis(1,1,2,2-Tetrahydroperfluorodecylthio)butane-1,4-di(hydroxy ethyl ether)

C$_8$F$_{17}$CH$_2$CH$_2$SCHCH$_2$O(CH$_2$CH$_2$O)$_n$H
|
C$_8$F$_{17}$CH$_2$CH$_2$SCHCH$_2$O(CH$_2$CH$_2$O)$_n$H
n=average 1

In a glass ampoule, 1,1,2,2-tetrahydroperfluorodecanethiol (15.4g; 0.033 mole) and 2-butyn-1,4-hydroxyethyl ether* (2.61g; 0.015 mole) were shaken and heated at 75° with 492 mg ABN for 18 hourss in 20 ml heptane. A waxy product was obtained which after removal of excess thiol, melted in the range 26° – 48°. Infrared examination confirmed the assigned structure, showing O-H stretching frequency at 3405 cm$^{-1}$. Nmr showed signals at 2.2 - 3.2 ppm SCH$_2$CH$_2$R$_f$ and 3.2 - 4.2 ppm —CHO(CH$_2$CH$_2$O)$_n$H with the correct integrals.

*A commercial product H(OCH$_2$CH$_2$)$_n$OCH$_2$C ≡ CCH$_2$O(CH$_2$C-H$_2$O)$_n$H, with n = 1 average, but actually being a mixture of at least five distinct compounds.

Elemental analysis:
Calculated for C$_{28}$H$_{24}$F$_{34}$O$_4$S$_2$ (average n = 1) C 29.64; H 2.13; F 56.9; Found: C 30.04; H 2.25; F 55.8.

EXAMPLE 15

2,3-Bis(1,1,2,2-Tetrahydroperfluorodecylthio)butyl-1,4-diacetate

C$_8$F$_{17}$CH$_2$CH$_2$SCHCH$_2$OCOCH$_3$
|
C$_8$F$_{17}$CH$_2$CH$_2$SCHCH$_2$OCOCH$_3$

In a similar manner as Example 14, 1,1,2,2-tetrahydroperfluorodecanethiol (15.84g; 0.033 mole) 2-butyn-1,4-diacetate (2.55g; 0.015 mole) and 492 mg azobisisobutyronitrile were heated at 75° for 19 hours to give 12.3g (67%) product boiling at 185° at 0.1 mm Hg. Infrared analysis (C=O stretching frequency at 1750 cm$^{-1}$ and the absence of all O—H frequency bands) and nmr examination confirmed the structure. Nmr showed signals at 2.3 - 3.2 ppm (8H) SCH$_2$CH$_2$; 3.45 ppm (2H) SCH; and 4.38 ppm (4H) OCH$_2$. The methyl protons resonated at 2.05 ppm.

Elemental Analysis: Calculated for C$_{28}$H$_{20}$F$_{34}$O$_4$S$_2$: C, 29.75 H, 1.78 F, 57.14; Found: C, 29.83 H, 1.78 F, 56.59.

EXAMPLE 16

2-(1,1,2,2-Tetrahydroperfluorodecylthio)-2-butene-1,4-diol

C$_8$F$_{17}$CH$_2$CH$_2$SCCH$_2$OH
||
CHCH$_2$OH 1,1,2,2-Tetrahydroperfluorodecanethiol (24g; 0.05 mole) was added slowly to a mixture of 2-butyn-1,4-diol (6.5g; 0.076 mole) in heptane, containing 820 mg ABN catalyst. This procedure gave a product enriched in the butenediol desired but also containing some of the diadduct (butanediol). The monoadduct butenediol was obtained in a pure state by sublimation at 150° and 0.7 mm Hg.

M.P. 87° – 89°. Nmr showed peaks at 2.2 – 3.2 ppm (4H) CH$_2$CH$_2$S; 3.8 ppm (2H) OH, 4.22 ppm (2H) S—C—CH$_2$O; 6.24 ppm (1H) =CH. The yield was 26%.

Elemental Analysis: Calculated for C$_{14}$H$_{11}$F$_{17}$O$_2$S: C, 29.69 H, 1.96 F, 57.03; Found: C, 29.49 H, 1.89 F, 56.71.

EXAMPLES 17 – 29

The following examples illustrate the wide variety of solvents which may be used in the reaction. All reactions were carried out with 1,1,2,2-tetrahydroperfluorodecanethiol (5.28g; 0.011 mole), 2-butyn-1,4-diol (0.43g; 0.005 mole) and 164 mg azobisisobutyronitrile. A reaction time of 18 hours at 76° was uniform for each example. Product analysis was made by gas chromatography. Since an excess of thiol was used, the results are given below in two sections. The first shows the thiol present in relation to the mono- and diadducts and is thus an indication of the suitability of the solvent. The second section shows the relative amounts of mono-adduct to di-adduct, without regard to the thiol present. In each case the mono-adduct is

C$_8$F$_{17}$CH$_2$CH$_2$SCCH$_2$OH
||
CHCH$_2$OH and the di-adduct is

C$_8$F$_{17}$CH$_2$CH$_2$SCHCH$_2$OH
|
C$_8$F$_{17}$CH$_2$CH$_2$SCHCH$_2$OH.

The results show that an inert, non-polar reaction medium, typically n-heptane, leads to maximum conversion of thiol and greatest production of di-adduct.

EXAMPLES 17 to 29

| Example | Solvent (10 ml) | G. C. Analysis (area %) | | | | |
|---|---|---|---|---|---|---|
| | | Thiol | Mono. | Di. | Mono | Di. |
| 17 | heptane | 12.4 | 0.8 | 86.6 | 0.9 | 99.1 |
| 18 | acetone*** | 55.0 | 17.4 | 27.6 | 38.7 | 61.3 |
| 19 | MEK | 51.2 | 18.9 | 29.9 | 38.8 | 61.2 |
| 20 | benzene | 24.7 | 23.0 | 52.3 | 26.9 | 73.1 |
| 21 | toluene | 23.4 | 24.4 | 52.2 | 31.8 | 68.2 |
| 22 | xylene | 24.2 | 21.5 | 54.3 | 28.4 | 71.6 |
| 23 | perchloroethylene* | 29.2 | 0 | 3.9 | — | — |
| 24 | carbon tetrachloride** | 18.7 | 3.8 | 44.9 | 7.8 | 92.2 |
| 25 | ethylene dichloride | 48.3 | 22.3 | 29.4 | 43.1 | 56.9 |
| 26 | ethyl acetate | 47.8 | 9.2 | 43.0 | 17.6 | 82.2 |
| 27 | t-butyl alcohol | 43.1 | 26.1 | 30.8 | 45.9 | 54.1 |
| 28 | methyl cellosolve | 39.0 | 19.3 | 41.7 | 31.6 | 68.0 |
| 29 | isopropyl alcohol | 44.7 | 27.1 | 28.2 | 49.0 | 51.0 |

*principal products were disulfide ($C_8F_{17}CH_2CH_2S$), accounting for 28.2% and three unidentified materials (total 38.7%)
**disulfide (32.6%) was major impurity
***reaction temperature 60°

EXAMPLES 30 to 36

Various free radical catalysts, in addition to ultraviolet irradiation, may be used to initiate the addition reaction. Below shows the effect of several different chemical initiators. Their effectiveness is judged by the amount of thiol consumed. In each reaction 1,1,2,2-tetrahydroperfluorodecanethiol (4.8g; 0.01 mole) and 2-butyn-1,4-diol were heated with the designated catalyst (10 mole % based on thiol). Heptane was used as a solvent except as indicated.

unidentified by-products. Thus the actual conversion of thiol to di-adduct in these cases is much lower than the actual thiol consumption.

EXAMPLES 37 to 45

Other examples of the radical catalyzed addition of $R_f$-thiol to commercial acetylenic alcohols and esters, using reaction conditions as shown in Example 2a are listed below.

Examples 37 to 45 illustrate additional combinations of $R_f$-thiols with acetylenic diols and esters. The reaction conditions are those of Example 2a.

| Example | Catalyst | Reaction Temp °C | Time Hrs. | Thiol Consumed |
|---|---|---|---|---|
| 30 | benzoyl peroxide | 90 | 18 | 45 |
| 31 | lauroyl peroxide | 85 | 18 | 42 |
| 32 | azo bisisobutyronitrile | 75 | 18 | 78 |
| 33 | 2-t-butyl azoisobutyronitrile | 100* | 17 | 75 |
| 34 | 1-1-butyl azo-1-cyano-cyclohexane | 117* | 17 | 76 |
| 35 | 2,5-dimethyl-2,5-di (t-butylperoxy) hexane | 130** | 20 | 28 |
| 36 | di-t-butyl peroxide | 140** | 20 | 33 |

*methyl isobutylketone solvent
**o-xylene solvent

All peroxides gave poor conversions of thiol to di-adduct and also gave rise to considerable amounts of

EXAMPLES 37 to 45

| Ex. | Thiol | Alcohol or Ester | Product |
|---|---|---|---|
| 37 | 2 $C_8F_{17}CH_2CH_2S$—<br>—$CH_2CH_2CH_2SH$ | + $HOCH_2C≡CCH_2OH$ → | $C_8F_{17}CH_2CH_2SCH_2CH_2CH_2SCHCH_2OH$<br>\|<br>$C_8F_{17}CH_2CH_2SCH_2CH_2CH_2SCHCH_2OH$ |
| 38 | 2 $C_8F_{17}CH_2CH_2S$—<br>—$CH_2CH_2CH_2SH$ | $H(OCH_2CH_2)_nOCH_2C≡CCH_2O(CH_2CH_2O)_nH$ → | $C_8F_{17}CH_2CH_2SCH_2CH_2CH_2SCHCH_2O(CH_2CH_2O)_nH$<br>\|<br>$C_8F_{17}CH_2CH_2SCH_2CH_2CH_2SCHCH_2O(CH_2CH_2O)_nH$<br>n = 1 average |
| 39 | 2 $C_8F_{17}CH_2CH_2S$—<br>—$CH_2CH_2CH_2SH$ | + $CH_3COOCH_2C≡CCH_2OCOCH_3$ → | $C_8F_{17}CH_2CH_2SCH_2CH_2CH_2CH_2SCHCH_2OCOCH_3$<br>\|<br>$C_8F_{17}CH_2CH_2SCH_2CH_2CH_2CH_2SCHCH_2OCOCH_3$ |
| 40 | 2 $C_8F_{17}CH_2CH_2O$—<br>—$CH_2CH_2CH_2SH$ | + $HOCH_2C≡CCH_2OH$ → | $C_8F_{17}CH_2CH_2OCH_2CH_2CH_2SCHCH_2OH$<br>\|<br>$C_8F_{17}CH_2CH_2OCH_2CH_2CH_2SCHCH_2OH$ |
| 41 | 2 $C_8F_{17}CH_2CH_2O$—<br>—$CH_2CH_2CH_2SH$ | + $H(OCH_2CH_2)_nOCH_2C≡CCH_2O(CH_2CH_2O)_nH$ → | |

-continued

EXAMPLES 37 to 45

| Ex. | Thiol | Alcohol or Ester | Product |
|---|---|---|---|
| | | | $C_8F_{17}CH_2CH_2OCH_2CH_2CH_2SCHCH_2O(CH_2CH_2O)_nH$ |
| | | | \| |
| | | | $C_8F_{17}CH_2CH_2OCH_2CH_2CH_2SCHCH_2O(CH_2CH_2O)_nH$ |
| | | | n= 1 average |
| 42 | 2 $C_8F_{17}CH_2CH_2O—$ $—CH_2CH_2CH_2SH$ | + $CH_3COOCH_2C\equiv CCH_2OCOCH_3 \rightarrow$ | $C_8F_{17}CH_2CH_2OCH_2CH_2CH_2SCHCH_2OCOCH_3$ \| $C_8F_{17}CH_2CH_2OCH_2CH_2CH_2SCHCH_2OCOCH_3$ |
| 43 | 2 $C_8F_{17}CH_2CH_2N—$ $—(CH_3)CH_2CH_2CH_2SH$ | + $HOCH_2C\equiv CCH_2OH \rightarrow$ | $C_8F_{17}CH_2CH_2N(CH_3)CH_2CH_2CH_2SCHCH_2OH$ \| $C_8F_{17}CH_2CH_2N(CH_3)CH_2CH_2CH_2SCHCH_2OH$ |
| 44 | 2 $C_8F_{17}CH_2CH_2N—$ $—(CH_3)CH_2CH_2CH_2SH$ | + $H(OCH_2CH_2)_nOCH_2C\equiv CCH_2O(CH_2CH_2O)_nH \rightarrow$ | $C_8F_{17}CH_2CH_2N(CH_3)CH_2CH_2CH_2SCHCH_2O(CH_2CH_2O)_nH$ \| $C_8F_{17}CH_2CH_2N(CH_3)CH_2CH_2CH_2SCHCH_2O(CH_2CH_2O)_nH$ |
| 45 | 2 $C_8F_{17}CH_2CH_2N—$ $—(CH_3)CH_2CH_2CH_2SH$ | + $CH_3COOCH_2C\equiv CCH_2OCOCH_3 \rightarrow$ | $C_8F_{17}CH_2CH_2N(CH_3)CH_2CH_2CH_2SCHCH_2OCOCH_3$ \| $C_8F_{17}CH_2CH_2N(CH_3)CH_2CH_2CH_2SCHCH_2OCOCH_3$ |

Examples 46 to 63 illustrate the conversion of the perfluoroalkylthioglycols described herein to fluorine-containing urethane compositions.

EXAMPLE 46

The diol of Example 1 (7.85 grams; 0.0075 mole) and Tonco 70 (a commercial mono-isocyanate containing 70% octadecyl isocyanate and 30% hexadecyl isocyanate) 4.31 grams; 0.05 mole) were dissolved in 20 ml urethane grade methyl ethyl ketone in a sealed reaction vessel. As a catalyst, 456 mg of a 1% solution of dibutyltindilaurate (7.5 × $10^{-6}$ moles catalyst) in MEK was added and the reactor was heated at 75°, with agitation, for 18 hours, when infrared examination showed all –NCO functionality to be absent (no stretching vibration at 2275 cm$^{-1}$). 11.3 grams of urethane was obtained as an amber wax by evaporation of the solvent. The product melted at 73° to 88°. The infrared spectrum showed N–H str. at 3335 cm$^{-1}$ and C=O str. at 1694 cm$^{-1}$.

Elemental Analysis: Calc'd: C, 45.06; H, 5.45; N, 1.73; F, 39.86; Found: C, 45.00; H, 5.41; N, 1.74; F, 39.69.

EXAMPLE 47

When the diol of Example 1 (7.85 grams; 0.0075 mole) and Desmodur RF [a commercial thiophosphoryl tris (4-phenylisocyanate)] (2.09 grams; 0.005 moles) are reacted according to the conditions of Example 46 there are obtained 8.0 grams of urethane product as a hard granular material.

Low molecular weight urethane compositions such as are described in Examples 46 and 47 are useful as coatings on vinyl surfaces to render the same soil repellent. The urethane composition can be applied from MEK solution to vinyl sheeting and the treated material resists soiling according to a standard test, in contrast to an untreated sample.

EXAMPLES 48 to 52

2,3-bis (1,1,2,2-tetrahydroperfluorodecylthio) butane-1,4-diol (the diol of Example 1) was converted by reaction with equimolar amounts of a diisocyanate to a high molecular weight urethane composition characterized by the presence of a segment of formula:

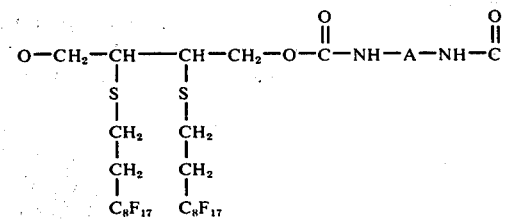

where A is the residue obtained from the indicated diisocyanate.

The $R_f$ glycol and the diisocyanate were dissolved in about 20 ml urethane grade methyl ethyl ketone in a sealed reaction vessel. The indicated amount of catalyst was added and the reactor heated for 17 hours at 73° C with agitation. The results are summarized below.

| Ex. | Weight | Moles | Isocyanate* | Weight | Mole | CATALYST** Wt.g 1% Soln. | Moles | Weight of Product (grams) | Elemental Calcd. | | Anal. Found | γc*** dynes/cm |
|---|---|---|---|---|---|---|---|---|---|---|---|---|
| 48 | 8.37 | 0.008 | DDI | 4.80 | 0.008 | 485 mg | 8×10$^{-6}$ | 6.0 | C | 45.53 | 45.98 | 12.66 |
| | | | | | | | | | H | 5.42 | 5.36 | |
| | | | | | | | | | N | 1.71 | 1.81 | |
| | | | | | | | | | F | 39.50 | 38.83 | |
| 49 | 10.46 | 0.010 | LDIM | 2.12 | 0.010 | 607 mg | 1×10$^{-5}$ | 10.0 | C | 31.49 | 31.85 | 11.88 |
| | | | | | | | | | H | 2.24 | 2.37 | |
| | | | | | | | | | F | 51.32 | 50.77 | |

-continued

| Ex. | Weight | Moles | Isocyanate* | Weight | Mole | CATALYST** Wt.g 1% Soln. | Moles | Weight of Product (grams) | Elemental Calcd. | | Anal. Found | $\gamma_c$*** dynes/cm |
|---|---|---|---|---|---|---|---|---|---|---|---|---|
| 50 | 11.51 | 0.011 | HDI | 1.85 | 0.011 | 688 mg | $1.1\times10^{-5}$ | 10.4 | C | 31.64 | 31.54 | 11.50 |
|  |  |  |  |  |  |  |  |  | H | 2.32 | 2.21 |  |
|  |  |  |  |  |  |  |  |  | F | 53.18 | 52.21 |  |
| 51 | 10.46 | 0.010 | TMDI | 2.10 | 0.010 | 607 mg | $1\times10^{-5}$ | 10 | C | 33.45 | 33.27 | 12.95 |
|  |  |  |  |  |  |  |  |  | H | 2.73 | 2.80 |  |
|  |  |  |  |  |  |  |  |  | F | 51.40 | 51.41 |  |
| 52 | 11.51 | 0.011 | TDI | 1.91 | 0.011 | 688 mg | $1.1\times10^{-5}$ | 10.2 | C | 32.47 | 32.67 | 12.66 |
|  |  |  |  |  |  |  |  |  | H | 1.82 | 1.85 |  |
|  |  |  |  |  |  |  |  |  | F | 52.92 | 52.74 |  |

*DDI = dimeracid derived isocyanate - Quaker Oats Company
LDIM = Lysinediisocyanate methyl ester - Merck and Company
TDI = toluene 2,4-diisocyanate
**catalyst dibutyltindilamate, 1% in MEK
***critical surface tension for wetting

EXAMPLE 53

A hydroxy terminated $R_f$-containing prepolymer was prepared as follows:

2,3-Bis(1,1,2,2-tetrahydroperfluorodecylthio)butane-1,4-diol (the diol of Example 1) (20 g; 0.0191 mole) was mixed with lysine diisocyanate methyl ester (2.7 g; 0.0127 mole) in 20 g. methylethyl ketone. Dibutyltindilaurate was added (23 mg; $3.82 \times 10^{-5}$ mole) to the resulting solution and the reaction vessel was heated to 75° with agitation until all isocyanate had reacted, as shown by the disappearance of the N=C=O band in the infrared. The solution was divided into two equal parts. One was used for Example 54. The other was poured into cold heptane to precipitate the urethane product. After drying, this portion weighed 21.0 g. Infrared showed peaks at 3480 cm$^{-1}$ (O—H str.); 3340 cm$^{-1}$ (N—H str.) and 1715 cm$^{-1}$ (C=O str.; ester and urethane).

Elemental Analysis: Calc'd for $C_{90}H_{72}F_{102}N_4O_{14}S_6$: C, 30.33; H, 2.04; N, 1.57; F, 54.38; Found: C, 30.61; H, 2.00; N, 1.67; F, 53.96.

EXAMPLE 54

The hydroxy-terminated $R_f$-containing prepolymer was converted into a urethane composition by reaction with additional diisocyanate and the reaction product capped by reaction with a monoalcohol.

The prepolymer of Example 53 was treated at 75° with further amounts of lysine diisocyanate (1.35 g; 0.0064 mole) to cap the free OH groups and the urethane was terminated by the addition of 2,3-bis(1,1,2,2-tetrahydroperfluorodecylthio) propan-1-ol (6.5 g; 0.0064 mole). Reaction was judged to be complete when no isocyanate peaks were visible in the infrared. The product was precipitated by pouring the MEK solution slowly into chilled heptane. After drying the final urethane weighed 28.9 g, and had a rubbery consistency. No OH stretching frequencies were visible in the infrared, but N—H stretching frequency was present at 3335 cm$^{-1}$ and C=O (ester and urethane) was a broad band centered at 1715 cm$^{-1}$.

Elemental Analysis for $C_{154}H_{124}F_{170}N_8O_{24}S_{10}$. Calculated: C, 30.72; H, 2.08; N, 1.86; F, 53.64; Found: C, 30.75; H, 2.10; N, 1.94; F, 52.95.

EXAMPLE 55

This example illustrates the formation of diisocyanate-terminated $R_f$-containing intermediate and the conversion thereof to a high and low (relative) molecular weight urethane compositions.

A. High molecular weight 2,3-Bis(1,1,2,2-tetrahydroperfluorodecylthio)butane-1,4-diol (the diol of Example 1) (57.33 g; 0.055 mole) was dissolved in 150 g methylethyl ketone. Lysine diisocyanate methyl ester (5.83 g; 0.0275 mole) was added, followed by 3.46 g of a 1% solution of dibutyl tin dilaurate as catalyst. The solution was heated under reflux and stirred in a nitrogen atmosphere for 2½ hours. Then dimer acid derived diisocyanate (DDI, available from The Quaker Oats Company) (33.0 g; 0.055 mole) was added and heating and stirring were continued for a further 3 hours. To complete the urethane formation the isocyanate capped intermediate was divided into two equal parts. The first was treated with lysine diisocyanate methyl ester (2.77 g; 0.013 mole) and N-methyl diethanolamine (3.11 g; 0.027 mole), to give a material which was purified by evaporation of the solvent followed by freeze drying from benzene. An infrared spectrum of the material showed N—H str. at 3336 cm$^{-1}$ and a broad carbonyl band (C=) str.) with a main peak at 1690 cm$^{-1}$, due to the ester and urethane linkages. The material was only sparingly soluble in methanol.

Elemental Analysis for $C_{152}H_{226}F_{68}N_{10}O_{20}S_4$. Calculated: C, 46.4; H, 5.8; F, 32.8; Found: C, 46.5; H, 5.6; F, 33.8. Critical surface tension for wetting, $\gamma_c = 11.32$ dynes/cm.

B. Low molecular weight

The second half of the isocyanate capped prepolymer was treated with lysine diisocyanate methyl ester (2.77 g; 0.013 mole) and N-methyldiethanolamine (3.67 g; 0.031 mole). The excess termination diol acts as a chain terminator and gives a lower molecular weight polyurethane. By freeze drying, a quantitative yield of polyurethane was obtained. The infrared spectrum and elemental analyses were similar to those of part A. The principal difference was that the low molecular weight urethane was very soluble in methanol, and could only be recovered in good yield by freeze drying from benzene.

Critical surface tension for wetting, $\gamma_c = 12.37$ dynes/cm.

EXAMPLE 56

A hydroxy-terminated $R_f$-containing prepolymer was prepared as follows:

Methyl ethyl ketone (600 g) was charged to a 2 l. flask fitted with a stirrer, thermometer, nitrogen inlet and a condenser protected with a drying tube. 2,3-Bis(1,1,2,2-tetrahydroperfluoroalkylthio)butane-1,4-diol (600 g; 0.571 mole)* was added together with a 1:1 mixture of 2,2,4-trimethylhexamethylene diisocyanate and 2,4,4-trimethylhexamethylenediisocyanate (80.16 g; 0.381 mole). All reagents were rinsed in with an additional 50 g MEK. The solution was heated to boiling and 50 g solvent was removed by distillation to effect azeotropic drying of all materials. Then dibutyltindilaurate (0.692 g; 1.14 × 10⁻³ mole; 2 mole % based on diol) was added as a catalyst and the solution was heated under reflux for 6 hours, when the reaction was judged to be complete by the absence of the N=C=O infrared band at 2270 cm⁻¹. The solution was cooled to room temperature (25°) and diluted with MEK to a total of 2042 g (33⅓% solids). A portion of the above material was taken to dryness. A quantitative recovery of a resinous material was obtained. Elemental analysis showed 52.8%F (theory: 53.4%F). Infrared bands at 3460 cm⁻¹ (O—H str.), 3340 cm⁻¹ (N—H str.) and 1705 cm⁻¹ (C=) str.) confirmed the structure of the hydroxy-terminated urethane prepolymer.

*The diol has the formula

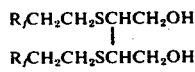

where $R_f$ is a mixture of prefluoroalkyl chains consisting of $C_6F_{13}$, $C_8F_{17}$ and $C_{10}F_{21}$. The diol is described in Example 2.

EXAMPLE 57

The hydroxy-terminated prepolymer of Example 56 (53.7 g solution, 17.9 g solids) was treated further at 75° with dimer acid derived diisocyanate (6.0 g; 0.01 mole) (DDI, Quaker Oats Company) for two hours, then the urethane chain was completed by the addition of trimethylhexamethylene diisocyanate (2,2,4 and 2,4,4 isomer mixture) (1.05 g; 0.005 mole) and N-methyldiethanolamine (1.19 g; 0.01 mole). Reaction was complete in three hours, as shown by the disappearance of the N=C=O band (2270 cm⁻¹) in the infrared spectrum. A sample taken to dryness gave a quantitative yield of an off-white powder containing 35.8%F (theory 36.6%F). For application to textile fabrics the polyurethane was applied either from solvent (MEK solution) or as an aqueous emulsion. The latter was made by first quaternizing the tertiary nitrogen atoms with glacial acetic acid and then pouring the MEK solution into a sufficient volume of water to give a clear emulsion.

EXAMPLE 58

The prepolymer of Example 56 (53.7 g solution; 17.9 g solids) was treated as in Example 57 with dimer acid derived isocyanate (6.0 g; 0.01 mole) (DDI, Quaker Oats Company) for 2 hours at 75° followed by further reaction with N-methyldiethanolamine (3.57 g; 0.03 mole) and dimer acid derived isocyanate (15.0 g; 0.025 mole) (DDI). Reaction was judged to be complete in 3 hours. An aliquot of the polyurethane solution was taken to dryness to yield a quantitative amount of off-white powder, containing 23.0%F (theory 22.4%). Application to fabrics was made either as a solvent based material or as a self-emulsifiable quaternized polyurethane as described in Example 57.

EXAMPLE 59

When the prepolymer of Example 56 (53.7 g solution; 17.9 g solids) is treated was dimer acid derived isocyanate (DDI) (6.0 g; 0.01 mole) for 2 hours at 75°; there is obtained an isocyanate terminated prepolymer. This is extended with 2,2-bis(hydroxy methyl)-propionic acid (1.34 g; 0.01 mole) and trimethylhexamethylene-diisocyanate (1.05 g; 0.005 mole). This acidic function is neutralized by the addition of potassium hydroxide and the product is self-emulsifiable when poured into water.

EXAMPLE 60

The utility of the urethane compositions of the preceding examples is illustrated below. The compositions were applied to fabrics at a loading of 0.08%F based on the weight of fabric (OWF) and tested for oil and water repellency.

The AATCC water spray test rating was determined according to Standard Test Method 22-1971 of the American Association of Textile Chemists and Colorists. Ratings are given from 0 (minimum) to 100 (maximum).

The AATCC Oil Rating was determined according to Standard Test Method 118-1972 of the American Association of Textile Chemists and Colorists. Ratings are given from 0 (minimum) to 8 (maximum). A commonly accepted lower value on soil repellent fabrics in the U.S. is an oil repellency of 4.

All mentioned AATCC Tests are listed in the Technical Manual of the American Association of Textile Chemists and Colorists, Volume 48, Edition 1972.

The novel urethane compositions were applied to polyester fabric, or polyester-cotton twill (65/35) in such a way that 0.08% fluorine was deposited onto the fabric. The cotton/polyester fabric is a 65% polyester-35% cotton blend. The polyester is one formed from ethylene glycol and terephthalic acid, sold for example under the Dacron trademark.

Polymers dissolved in a non-aqueous medium were mostly applied to fabric by a padding process and were evaluated after air drying and after curing in a hot air oven at >150° C for 3 minutes.

| Evaluation of Polyurethanes as Oil and Water Repellents Applied at a Level of 0.08% OWF | | | |
|---|---|---|---|
| Urethane of Example | Oil Repellency | Water Repellency | Fabric* |
| 46 | 0–1 | 0 | Cotton/PE |
| 49 | 5–6 | 80 | PE |
| 50 | 6 | 80 | '' |
| 51 | 6 | 80 | '' |
| 52 | 1 | 80 | '' |
| 53 | 5 | 0 | Cotton/PE |
| 54 | 4–5 | 70 | '' |
| 55A | 3 | 70 | '' |
| 55B | 3 | 70+ | '' |
| 57 | 6 | 80 | '' |
| 58 | 6 | 80+ | '' |

*Cotton/PE = 35% cotton, 65% polyester  PE = 100% polyester

EXAMPLE 61

Incorporation of small amounts of $R_f$-glycol into polyurethane elastomer compositions imparts excellent release properties to molds made from the elastomer. The $R_f$-glycol itself contains 60%F, but incorporation of only enough $R_f$-glycol to give the final formulation of 0.6%F is sufficient to produce the desired mold release properties.

2,3-Bis(1,1,2,2-tetrahydroperfluoroalkylthio)butane-1,4-diol (47 g; 0.046 mole) the diol of Example 1, and tolylene-2,4-diisocyanate (322 g; 1.85 mole) were mixed and allowed to react at 80° for 30 minutes. This gave a solution of fluorinated diisocyanate prepolymer in excess TDI. To this solution was added Polymeg 1000* (521 g) and Pluracol 2010** (573 g), keeping the temperature below 50° with external cooling. Then the reaction was completed by heating at 82° for 2 hours to give an isocyanate capped polymer containing approximately 10% NCO. The fluorine content of the polymer was approximately 2% and its free surface energy, $\gamma_c$ was 12 dynes/cm.

*Quaker Oats Company: Polytetramethylene ether glycol
** BASF-Wyandotte: Polypropylene glycol This material was blended with a polymer made without the addition of $R_f$-diol, such that the final fluorine content was 0.6%. Molds made from this blend exhibited excellent release properties. Molds made from non-fluorine containing polymers caused considerable sticking of molded parts.

EXAMPLE 62

Polyurethane varnishes are well-known commercial items. Generally, they provide clear coatings with excellent mechanical and solvent resistant properties. By incorporating a small amount of $R_f$-glycol (sufficient to give as little as 0.5%F in the final film) the general polyurethane properties are not impaired and the incorporated fluorine allows better wetting of the surfaces to be coated by the varnish. The final, hard fluorine containing film has a critical surface energy $\gamma_c$ of ~12 dynes/cm, which means that it cannot be wetted by most common liquids and that it is therefore more soil resistant than ordinary polyurethane coatings.

2,3-Bis(1,1,2,2-tetrahydroperfluoroalkylthio)butane-1,4-diol (0.1 mole) the diol of Example 2 is reacted with 3.2 mole tolylene-2,4-diisocyanate to give fluorinated isocyanate propolymer. This is then mixed with tris-(hydroxymethyl) propane (1 mole) and warmed to complete reaction.

A commercial hydroxyl terminated polyester (Desmophen 800) (17.3 parts by volume) is dissolved in a standard polyurethane solvent (glycolmonomethylether acetate, butyl acetate, ethyl acetate and toluene) and to the solution is added 41.5 parts by volume of the isocyanate capped polymer described above, and well mixed. The solution is then ready for brushing or spraying on the surface to be coated, hardens to a clear varnish after a few hours exposure at ambient conditions.

Fiber reactivity of the polyurethanes can be achieved through a —NCO terminated polymer. Application of such a material from a non-reactive solvent (e.g., trichloroethane) to a cellulosic fiber, followed by a high temperature cure results in a urethane bond formation between the —OH groups of the fiber and the —NCO groups of the polymer. Alternatively, cross-linking may be achieved between the polymer chains by reaction of the terminal —NCO groups with already formed urethane linkages, to give allophanate structures.

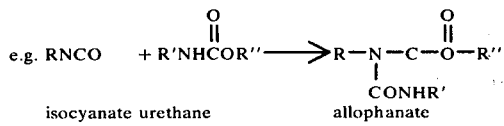

e.g. RNCO + R'NHCOR'' ⟶ R—N—C—O—R''
                              |
                          CONHR' isocyanate   urethane                    allophanate

Another alternative is for a conventional hydroxyl terminated polymer, as previously exemplified, to be co-applied, from solvent, with a fiber-reactive resin, such as a polymethylolmelamine, which will react, on curing, with the —OH groups of both the fiber and the polyurethane.

EXAMPLE 63

Methyl ethyl ketone (600 g) is charged to a 2 l. flask fitted with a stirrer, thermometer, nitrogen inlet and a condenser protected with a drying tube. 2,3-bis (1,1,2,2-tetrahydroperfluoroalkylthio)butane 1,4-diol (600 g; 0.571 mole) the diol of Example 2, is added together with a 1:1 mixture of 2,2,4-trimethylhexamethylene diisocyanate and 2,4,4-trimethylhexamethylenediisocyanate (80.16 g; 0.381 mole). All reagents are rinsed in with an additional 50 g MEK. The solution is heated to boiling and 50 g solvent are removed by distillation to effect azeotropic drying of all materials. Then dibutyltindilaurate (0.692 g; 1.14 × $10^{-3}$ mole; 2 mole % based on diol) is added as a catalyst and the solution heated under reflux for six hours. At the end of this time the reaction is judged to be complete by the absence of the N=C=O infrared band at 2270 $cm^{-1}$. A further 800 ml of MEK are added and the hydroxyl terminated prepolymer treated further with dimer acid derived diisocyanate (228.6 g; 0.381 mole) (DDI) for two hours. The urethane chain is completed by the addition of further dimer acid derived diisocyanate (457.6 g; 0.762 mole) (DDI) and 1,4-butanediol (68.5 g; 0.762 mole).

The presence of —NCO bands in the final product is shown by infrared adsorption (2270 $cm^{-1}$). Addition of 1450 ml MEK gave a product containing 33½% solids. This product is applied to fabrics by application from solvent by diluting the concentrate with 1,1,1-trichloroethane such that the treating bath contains approximately 0.2%F. Fabrics so treated typically exhibit an oil repellency of 6 and a water spray rating of 80.

EXAMPLE 64

This example illustrates the conversion of a perfluoroalkylalkyl ene iodide to the corresponding thiol by reaction with thiourea.

In a 1 liter flask is place 100 g (0.138 mole) of $C_{11}F_{23}CH_2CH_2I$, 12.6 (0.166 mole) of thiourea and 100 ml of anhydrous ethanol and the mixture is refluxed for 5 hours. Then about 50 ml of the ethanol is stripped off under vacuum and 400 ml $H_2O$ and 11.04 g (0.138 mole) of 50% aqueous NaOH are added and the reaction mixture is boiled.

The mercaptan, $C_{11}F_{23}CH_2CH_2SH$, is collected in a Dean-Stark trap as a lower layer in good yield.

EXAMPLE 65

This example illustrates two alternate synthetic methods for preparing the thiol $R_f — R_1 — SH$ A. Reaction of $R_f — CH = CH_2$ with $H_2S$.

The olefin $C_9F_{19}CH = CH_2$ is reacted with $H_2S$ at +5° C at 200 PSIG $H_2S$, the mole ratio of $H_2S$ to olefin being about 30:1 in a water jacketed quartz tube irradiated with the ultraviolet light furnished by two 36" germicidal lamps under static conditions. The major product is:

$C_9F_{17}CH_2CH_2SH$

B. Reaction of $R_fCH_2CH_2I$ with thiourea followed by hydrolysis.

In a 5 liter round bottom flask equipped with a water cooled condenser, stirrer and heating mantle is placed 624 g (1.0 mole) of $(CF_3)_2 CF(CF_2)_6CH_2CH_2I$, 114 g thiourea (1.5 mole) and 3 liters of absolute ethanol. The reaction mixture is heated at reflux for 26 hours. Ethanol is then removed while adding water to maintain constant volume. 200 ml of 1M NaOH is then added and the solution co-distilled with water into a phase separator. The aqueous phase is returned to the reaction vessel. Further distillation gives the pure mercaptan $$(CF_3)_2CF(CF_2)_nCH_2CH_2SH.$$

What I claim is:

1. A compound of the formula $$R_f-R_1-S-CH-R_2-O-R_4$$
$$\phantom{R_f-R_1-S-CH-}|$$
$$R_f-R_1-S-CH-R_3-O-R_4$$

in which $R_f$ is straight or branched-chain perfluoroalkyl of 1 to 18 carbon atoms or said perfluoroalkyl substituted by perfluoroalkoxy of 2 to 6 carbon atoms;

$R_1$ is branched or straight chain alkylene of 1 12 carbon atoms, alkylenethioalkylene of 2 to 12 carbon atoms, or alkyleneoxyalkylene of 2 to 12 carbon atoms;

$R_2$ and $R_3$ each independently is straight or branched chain alkylene of 1 to 12 carbon atoms; straight or branched chain alkylene of 1 to 12 carbon atoms, substituted by one or two of phenyl or cyclohexyl; or $R_2$ and $R_3$ are a group of the formula $$C_mH_{2m}(OC_kH_{2k})_r$$

where $m$ is an integer from 1 to 12,
$k$ is an integer from 2 to 6,
$r$ is an integer from 1 to 40
$R_4$ is alkanoyl of 1 to 24 carbon atoms, alkenoyl of 1 to 24 carbon atoms or said alkanoyl or alkenoyl substituted by 1 to 3 of chloro, bromo and carboxyl,
or said alkanoyl substituted by phenyl or naphthyl, said phenyl or naphthyl being unsubstituted or substituted by 1 to 3 of chloro, bromo, alkyl of 1 to 6 carbon atoms, alkoxy of 1 to 6 carbon atoms,
or said alkanoyl substituted by lower acyl or lower acylamino where lower acyl means alkanoyl or alkenoyl of 2 to 6 carbon atoms and the mono- or di-chloro or bromo derivative thereof;
or $R_4$ is benzoyl or benzoyl substituted by 1 to 3 of chloro, bromo, alkyl of 1 to 18 carbon atoms, alkoxy of 1 to 8 carbon atoms or lower acyl or lower acylamino where lower acyl means alkanoyl or alkenoyl of 2 to 6 carbon atoms, and the mono- or di-chloro or bromo derivative thereof.

2. A compound according to claim 1 in which
$R_f$ is perfluoroalkyl of 6 to 12 carbon atoms or said perfluoroalkyl substituted by perfluoroalkoxy of 2 to 6 carbon atoms;
$R_1$ is branched or straight chain alkylene of 2 to 8 carbon atoms, alkylenethioalkylene of 2 to 8 carbon atoms, or alkyleneoxyalkylene of 2 to 8 carbon atoms;
$R_2$ and $R_3$ are each independently straight or branched chain alkylene of 1 to 4 carbon atoms or a group of formula $$C_mH_{2m}(OC_kH_{2k})_r$$

where
$m$ is an integer from 1 tp 4,
$k$ is an integer from 2 to 4,
$r$ is an integer from 1 to 20,
$R_4$ is alkanoyl of 1 to 24 carbon atoms; alkanoyl of 1 to 6 carbon atoms substituted by phenyl; benzoyl, benzoyl substituted by alkyl of 1 to 6 carbon atoms; or $R_4$ is selected from chloroacetyl, bromoacetyl, $\beta$-chloropropionyl, $\beta$-bromopropionyl, $\alpha,\beta$-dichloropropionyl, $\alpha,\beta$-dibromopropionyl, acryl, methacryl, $\alpha$-chloroacryl, $\alpha$-bromoacryl, $\alpha,\beta$- or $\beta,\beta$-dichloro or dibromoacryl, $\beta$-chlorocrotonyl, $\alpha$-chlorocrotonyl, $\beta$-bromocrotonyl, or $\alpha$-bromocrotonyl.

3. A compound according to claim 1, in which
$R_f$ is perfluoroalkyl of 6 to 12 carbon atoms,
$R_1$ is alkylene of 2 to 4 carbon atoms,
$R_2$ and $R_3$ are both alkylene of 1 or 2 carbon atoms,
$R_4$ is alkanoyl of 6 to 18 carbon atoms.

4. A compound according to claim 1 of the formula $$R_f-CH_2CH_2SCHCH_2OR_4$$
$$\phantom{R_f-CH_2CH_2SCHCH_2OR_4}|$$
$$R_f-CH_2CH_2SCHCH_2OR_4$$

where
$R_f$ is perfluoroalkyl of 6 to 12 carbon atoms, and
$R_4$ is acetyl, or methacrylyl.

5. A compound according to claim 1 of the formula $$C_8F_{17}CH_2CH_2SCHCH_2OR_4$$
$$\phantom{C_8F_{17}CH_2CH_2SCHCH_2OR_4}|$$
$$C_8F_{17}CH_2CH_2SCHCH_2OR_4$$

where $R_4$ is acetyl, or methacrylyl.

6. A compound according to claim 1 of formula $$R_f-CH_2CH_2SCHCH_2OR_4$$
$$\phantom{R_f-CH_2CH_2SCHCH_2OR_4}|$$
$$R_f-CH_2CH_2SCHCH_2OR_4$$

where
$R_f$ is perfluoroalkoxyperfluoroalkyl of 4 to 12 carbon atoms, and
$R_4$ is acetyl, or methacrylyl.

7. A compound according to claim 1 of formula $$(CF_3)_2CFO(CF_2CF_2)_yCH_2CH_2SCHCH_2OR_4$$
$$\phantom{(CF_3)_2CFO(CF_2CF_2)_yCH_2CH_2SCHCH_2OR_4}|$$
$$(CF_3)_2CFO(CF_2CF_2)_yCH_2CH_2SCHCH_2OR_4$$

where
$y$ is an integer from 1 to 6, and
$R_4$ is acetyl, or methacrylyl.

8. A compound according to claim 6 of formula $$(CF_3)_2CFO(CF_2CF_2)_yCH_2CH_2SCHCH_2OR_4$$
$$\phantom{(CF_3)_2CFO(CF_2CF_2)_yCH_2CH_2SCHCH_2OR_4}|$$
$$(CF_3)_2CFO(CF_2CF_2)_yCH_2CH_2SCHCH_2OR_4$$

where
$y$ is 2, 3 or 4, and
$R_4$ is acetyl, or methacrylyl.

9. A compound according to claim 1 of formula

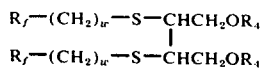

where
R*f* is perfluoroalkyl of 6 to 12 carbon atoms,
w is an integer from 1 to 8, and
R₄ is acetyl, or methacrylyl.

10. A compound according to claim 1 of formula

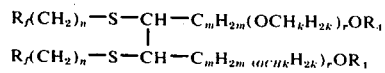

where
R*f* is perfluoroalkyl of 6 to 12 carbon atoms, $n$ is an integer from 1 to 12,
$m$ is an integer from 1 to 4,
$k$ is an integer from 2 to 4,
$r$ is an integer from 1 to 20, and
R₄ is acetyl, or methacrylyl.

11. A compound according to claim 10 of formula

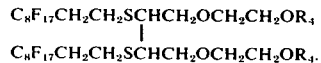

12. A compound according to claim 1 of formula

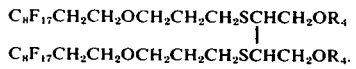

* * * * *

UNITED STATES PATENT AND TRADEMARK OFFICE
CERTIFICATE OF CORRECTION

PATENT NO. : 4,001,305
DATED : January 4, 1977
INVENTOR(S) : ROBERT ERNEST ARTHUR DEAR ET AL It is certified that error appears in the above-identified patent and that said Letters Patent are hereby corrected as shown below:

In column 37, claim 1, line 23, change "1  12" to -- 1 to 12 --.

In column 38, claim 2, line 4, change " 1 tp 4" to -- 1 to 4 --.

Signed and Sealed this

Nineteenth Day of April 1977

[SEAL]

Attest:

RUTH C. MASON
*Attesting Officer*

C. MARSHALL DANN
*Commissioner of Patents and Trademarks*